US010265303B2

(12) United States Patent
Martinez et al.

(10) Patent No.: US 10,265,303 B2
(45) Date of Patent: Apr. 23, 2019

(54) HYPERPHENYLALANINEMIA AND TREATMENTS THEREOF

(71) Applicant: BERGEN TEKNOLOGIOVERFØRING AS, Bergen (NO)

(72) Inventors: Aurora Martinez, Eidsvågneset (NO); Oscar Aubi Catevilla, Bergen (NO); Lars Skjærven, Bergen (NO); Jarl Underhaug, Bergen (NO); Ming Ying, Bergen (NO); Knut Teigen, Bergen (NO)

(73) Assignee: BERGEN TEKNOLOGIOVERFØRING AS, Bergen (NO)

( * ) Notice: Subject to any disclaimer, the term of this patent is extended or adjusted under 35 U.S.C. 154(b) by 0 days.

(21) Appl. No.: 15/752,454

(22) PCT Filed: Aug. 11, 2016

(86) PCT No.: PCT/EP2016/069184
§ 371 (c)(1),
(2) Date: Feb. 13, 2018

(87) PCT Pub. No.: WO2017/029202
PCT Pub. Date: Feb. 23, 2017

(65) Prior Publication Data
US 2019/0008839 A1 Jan. 10, 2019

(30) Foreign Application Priority Data
Aug. 14, 2015 (GB) .................................. 1514489.2

(51) Int. Cl.
A61K 31/44 (2006.01)
A61P 3/00 (2006.01)
A61K 31/506 (2006.01)
A61K 31/522 (2006.01)
A61K 45/06 (2006.01)

(52) U.S. Cl.
CPC ............ A61K 31/44 (2013.01); A61K 31/506 (2013.01); A61K 31/522 (2013.01); A61P 3/00 (2018.01); A61K 45/06 (2013.01); A61K 2300/00 (2013.01)

(58) Field of Classification Search
CPC .... A61K 31/44; A61K 31/506; A61K 31/522; A61K 45/06; A61P 3/00
USPC ........................................................ 514/275
See application file for complete search history.

(56) References Cited

U.S. PATENT DOCUMENTS

2010/0286166 A1* 11/2010 Pey Rodriguez .... A61K 31/42
514/254.05

FOREIGN PATENT DOCUMENTS

| EP | 2008656 A1 | 12/2008 |
| JP | 2009298754 A | 12/2009 |
| WO | 2009/000552 A2 | 12/2008 |
| WO | 2009/143049 A1 | 11/2009 |
| WO | 2010/057006 A9 | 9/2010 |
| WO | 2011/062885 A1 | 5/2011 |

OTHER PUBLICATIONS

Wettstein et al., "Linking genotypes database with locus-specific database and genotype—phenotype correlation in phenylketonuria", European Journal of Human Genetics (2015) 23(3): pp. 302-309.
Pey et al., "Mechanisms Underlying Responsiveness to Tetrahydrobiopterin in Mild Phenylketonuria Mutations", Human Mutation, 2004. 24(5): pp. 388-399.
Pey et al., "Identification of pharmacological chaperones as potential therapeutic agents to treat phenylketonuria", The Journal of Clinical Investigation, 2008. 118(8): pp. 2858-2867.
Martinez et al., "Expression of recombinant human phenylalanine hydroxylase as fusion protein in Escherichia coli circumvents proteolytic degradation by host cell proteases, Isolation and characterization of the wild-type enzyme", Biochem. J., 1995. 306: pp. 589-597.
Woody et al., "Adverse Effects of Trimethoprim-sulfamethoxazole in a Child with Dhydropteridine Reductase Deficiency", Development Medicine and Child Neurology, 1990, 32, pp. 639-642.
Werner et al., "Tetrahydrobiopterin: biochemistry and pathophysiology", Biochem. J. (2011), 438, pp. 397-414.
Andrews et al., "Effect of Cotrimoxazole on the Response to Phenylalanine Loading in Man", Clinica Chimica Acta, 68 (1976), pp. 17-30.
Leidenheimer et al., "Pharmacological Chaperoning: A Primer on Mechanism and Pharmacology", Pharmacol Res, 2014. 83: pp. 10-19.
Underhaug et al., "Phenylalanine Hydroxylase Misfolding and Pharmacological Chaperones", Current topics in medicinal chemistry, 2012. 12(22): pp. 2534-2545.
Calvo et al., "Effect of pharmacological chaperones on brain tyrosine hydroxylase and tryptophan hydroxylase 2", J. Neurochem., 2010, 114(3), pp. 853-863.
Hole et al., "Erratum to "Discovery of compounds that protect tyrosine hydroxylase activity through different mechanisms"", Biochim Biophys Acta, 2015.
Hawser et al., "Dihydrofolate reductase inhibitors as antibacterial agents", Biochem Pharmacol, 2006. 71(7): pp. 941-948.
Baker et al., "The Binding of Trimethoprim to Bacterial Dihydrofolate Reductase", FEBS Letters, 1981, 126(1): pp. 49-52.
Watts et al., "A new variant form of phenylketonuria", US National Library of Medicine (NLM), Bethesda, MD, US, Jul. 1979 XP002762814, Database accession No. NLM317358 Abstract.

(Continued)

Primary Examiner — Yevgeny Valenrod
(74) Attorney, Agent, or Firm — Fox Rothschild LLP

(57) ABSTRACT

The present invention relates to compounds of formula (I) as defined in the specification for use as pharmacological chaperones having a stabilizing effect on phenylalanine hydroxylase (PAH) for the treatment of hyperphenylalaninemia (HPA), in particular phenylketonuria (PKU). The compounds include trimethoprim and analogues and derivatives thereof.

22 Claims, 15 Drawing Sheets

(56) References Cited

OTHER PUBLICATIONS

Figure 1:
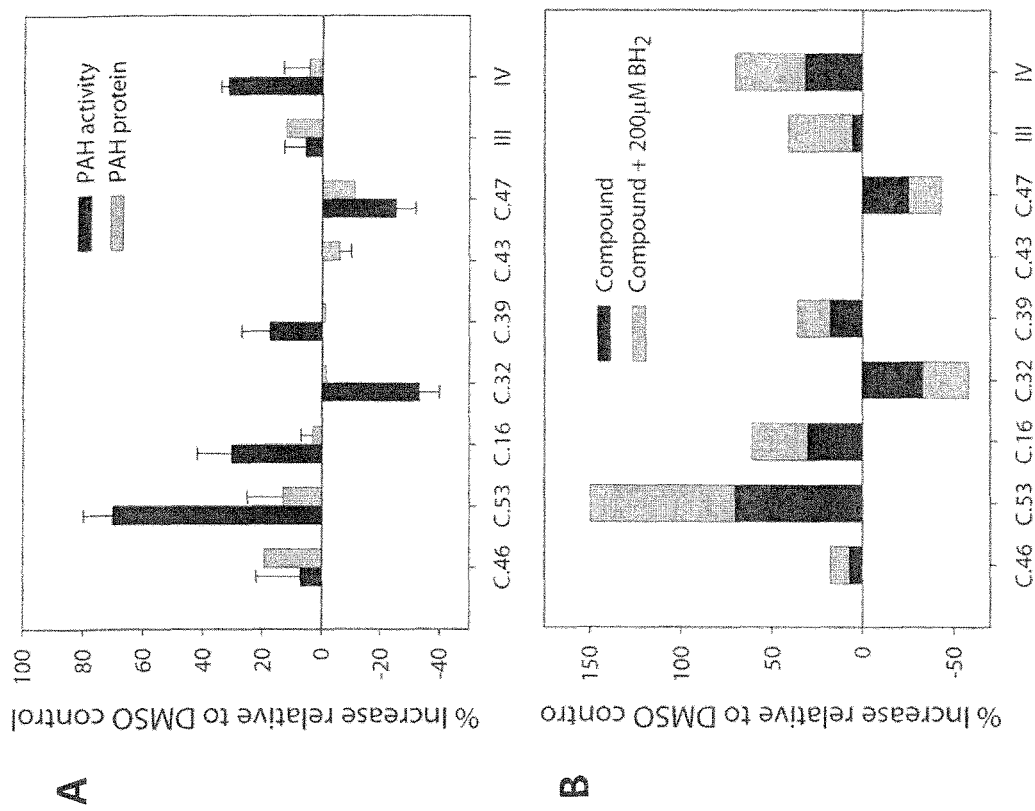

Watts et al., "A New Variant Form of Phenylketonuria", The Quarterly Journal of Medicine, 1979, vol. 48, No. 191, pp. 103-417.
Angel et al., "Identification of pharmacological chaperones as potential therapeutic agents to treat phenylketonuria", Journal of Clinical Investigation, vol. 118, No. 8, 2008, pp. 2858-2867.
Santos-Sierra et al., "Novel pharmacological chaperones that correct phenylketonuria in mice", Human Molecular Genetics, vol. 21, No. 8, 2012, pp. 1877-1887.
Aymami et al., "Pharmacological chaperones for enzyme enhancement therapy in genetic diseases", Pharmaceutical Patent Analyst, 2013, 2(1), pp. 109-124.
Database Medline [Online], US National Library of Medicine (NLM), Bethesda, MD, US; Jul. 1979, Watts R W et al: "A new variant form of phenylketonuria.", XP002762814, Database accession No. NLM317358 abstract, The Quarterly Journal of Medicine, vol. 48, No. 191, pp. 403-417.
Angel L. Pey et al: "Identification of pharmacological chaperones as potential therapeutic agents to treat phenylketonuria", Journal of Clinical Investigation, vol. 118, No. 8, Aug. 1, 2008, pp. 2858-2867, XP055308927, US.
S. Santos-Sierra et al: "Novel pharmacological chaperones that correct phenylketonuria in mice", Human Molecular Genetics, vol. 21, No. 8, Jan. 13, 2012, pp. 1877-1887, XP55309629, gb.

* cited by examiner

| D | Condition | $V_{max}$ (µmol/mg/min) | $S_{0.5}/K_m$ (µM) | Hill coef. ($h$) |
|---|---|---|---|---|
| Full-length tetrameric hPAH (panels A,B) | | | | |
| | Phe | | | |
| | Variable Phe, DMSO Control | 12.3±0.3 | 143.8±7.5 | 2.44±0.21 |
| | Variable Phe, + compound 53 | 12.5±0.3 | 140.1±6.2 | 2.47±0.18 |
| | BH$_4$ | | | |
| | Variable BH$_4$, control | 16.9±0.6 | 36.7±4.7 | |
| | Variable BH$_4$, + compound 53 | 11.8±0.6** | 17.5±3.6** | |
| Truncated ΔN102/ΔC24-hPAH | | | | |
| | BH$_4$ | | | |
| | Variable BH$_4$, DMSO control | 10.9±0.6 | 20.9±4.8 | |
| | Variable BH$_4$ + compound 53 | 10.9±0.7 | 20.5±5.4 | |

Figure 3 cont c53.10 c53.16 c53.17 c53.18 c53.19 c53.20 c53.21 c53.22

Compound 53.14

Compound 53.23

Compound 53.32

Compound 53.35

Compound 53.39

Compound 53.33

Compound 53.37

Compound 53.40

Compound 53.34

Compound 53.38

Compound 53.41

HYPERPHENYLALANINEMIA AND TREATMENTS THEREOF

The present invention relates to compounds for use in the treatment of hyperphenylalaninemia (HPA), in particular phenylketonuria (PKU). These compounds act as pharmacological chaperones of the enzyme phenylalanine hydroxylase.

Phenylalanine hydroxylase (PAH, EC 1.14.16.1) catalyzes the tetrahydrobiopterin ($BH_4$)-dependent conversion of L-phenylalanine (L-Phe) to L-tyrosine (L-Tyr). This is the initial and the rate-limiting step in phenylalanine catabolism, consuming in humans about 75% of the phenylalanine input from the diet. PAH is primarily present in the liver, where removal of excess L-Phe occurs. Mutations in the human PAH gene lead to increased neurotoxic levels of L-Phe in the blood and to the appearance in urine of metabolites that arise from the transamination of L-Phe to phenylpyruvate. This is the hallmark of the HPAs, of which PKU (OMIM 261600) is the most severe. About 13 000 new patients are diagnosed with PKU each year (averaged figures worldwide 1:10 000).

PKU patients are normally classified in three (phenotypic) groups depending on their off-diet blood phenylalanine (Phe) levels; mild HPA (MHP; 120-600 µmol/l), mild PKU (600-1200 µmol/l) and classic PKU (≥1200 µmol/l). Most PAH variants are missense variants (58.5%), followed by deletions (15.9%), splice-site variants (13.7%), nonsense variants (6.0%) and insertions (3.1%). Missense mutations, as well as small deletions and insertions are mainly associated with PAH misfolding and instability. Wettstein, S et al. in Eur. J. Hum. Genet., 2015, 23 (3): pp 302-9 describes the association of mutations with particular patient groups. The intracellular quality control mechanisms eliminate the defective mutant proteins via degradation through polyubiquitin-dependent processes such as proteasome-mediated degradation and/or selective autophagy, resulting in a partial or complete lack of associated PAH function.

The accumulation of Phe in blood and the brain and the subsequent disturbance in brain neurotransmitters lead to neurological symptoms including mental retardation, purposeless movements and depression. The dietary intake of Phe must therefore be strictly controlled in PKU patients and the established treatment is a Phe-restricted diet and, recently, supplementation with preparations of the natural $BH_4$ cofactor (i.e. the FDA-approved Kuvan®) also shows effectiveness for about 20-30% patients, who can follow a less strict Phe-free diet. $BH_4$ acts to increase PAH activity as it is one of the cosubstrates in the reaction (the "Michaelis-Menten" effect). In addition it has a PAH stabilizing, chaperone effect [Pey, A. L., et al., Hum. Mutat., 2004. 24 (5): p. 388-399].

Pharmacological chaperones are the focus of increasing interest as an approach with therapeutic potential aiming to correct protein misfolding. The decrease in PAH protein stability is the main molecular pathogenic mechanism in PKU. In 2008 we demonstrated the proof of the pharmacological chaperone concept for stabilizing PKU mutations with compounds found through screening [Pey, A. L., et al., J. Clin. Invest., 2008. 118 (8): p. 2858-67]. The compounds from this first study were later shown to be rather insoluble and that also affected the other neuronal aromatic amino acid hydroxylases, tyrosine hydroxylase (TH) and tryptophan hydroxylase 2 (TPH2). Thus, a need remains for an improved method of treating HPA and PKU.

The present inventors have identified a new class of compounds acting as pharmacological chaperones, preferably specific for PAH within the aromatic amino acid hydroxylases and, in preferred embodiments, with higher solubility than the compounds disclosed in Pey et al., 2008 (supra). The compounds stabilize PAH and many disease-associated mutations thereof and can increase PAH activity in cells expressing the enzyme. Furthermore, these compounds have a superior (and generally additive) effect to $BH_4$, allowing for possible combined treatment with the established administration of Kuvan®.

According to one aspect, the present invention provides a compound of formula (I)

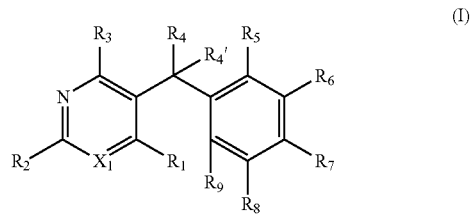

(I)

in which
$X_1$ is C or N;
$R_1$, $R_2$, and $R_3$, which may be the same or different, are selected from the group consisting of H, $NH_2$, OH, CN, $NO_2$, SH, halogen, optionally substituted $C_1$-$C_6$ alkyl or $C_2$-$C_6$ alkenyl, optionally substituted $C_1$-$C_6$ heteroalkyl wherein the heteroatoms are one or more N, O or S, optionally substituted $C_1$-$C_6$ thiol, optionally oxidized to —S(O)— or —S(O)$_2$—, optionally substituted $C_1$-$C_6$ aminoalkyl, optionally substituted $C_1$-$C_6$ alkoxy, $(Y)_p CO(Z)_q R_A$ and an aromatic group, optionally containing one or more heteroatoms selected from O, N and S, said aromatic group being optionally substituted, wherein Y and Z are independently selected from O and $N(R_B)$, p and q are independently 0 or 1, $R_A$ is selected from the group consisting of H, optionally substituted $C_1$-$C_6$ alkyl or $C_2$-$C_6$ alkenyl, and optionally substituted $C_1$-$C_6$ heteroalkyl wherein the heteroatoms are one or more N, O or S, and $R_B$ is selected from H and $C_1$-$C_3$ alkyl or cycloalkyl; and $R_4$ and $R_4'$ are independently selected from H, F, optionally substituted $C_1$-$C_6$ alkyl or $C_2$-$C_6$ alkenyl, optionally substituted phenyl or a 5- or 6-membered heteroaryl group or are fused to form a 3-6 membered aliphatic cyclic group which may contain one or more heteroatoms selected from N, O and S or together form =O or =S; or $R_1$ and $R_2$ are as defined above and $R_3$ and $R_4$ are fused to form a 5- or 6-membered ring, preferably a 6-membered ring, and thereby a compound of formula IIa

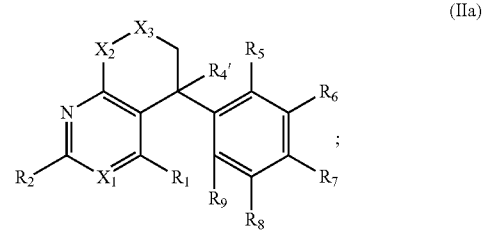

(IIa)

or $R_3$ and $R_2$ are as defined above and $R_1$ and $R_4$ are fused to form a 5- or 6-membered ring, preferably a 6-membered ring, and thereby a compound of formula IIb

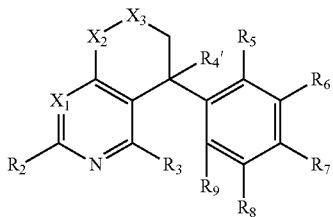

(IIb)

in which

X$_2$ is NR$_{10}$, O or S, wherein R$_{10}$ is H or C$_{1-3}$ alkyl which may be partially or fully fluorinated; and X$_3$ is a single or double bond, —CO—, —SO$_2$ or —CH$_2$—;

R$_5$, R$_6$, R$_7$, R$_8$ and R$_9$, which may be the same or different, are selected from the group consisting of H, OH, SH, halogen, CN, NO$_2$, NH$_2$, optionally substituted C$_1$-C$_6$ alkyl, optionally substituted C$_2$-C$_6$ alkenyl, optionally substituted C$_1$-C$_6$ aminoalkyl, optionally substituted C$_1$-C$_6$ heteroalkyl wherein the hetero atom is N, O or S, optionally substituted C$_1$-C$_6$ alkoxy, optionally substituted benzyloxy, optionally substituted C$_1$-C$_6$ thiol, optionally oxidized to —S(O)— or —S(O)$_2$—, and an aromatic group, optionally containing one or more heteroatoms selected from O, N and S, said aromatic group being optionally substituted, two of R$_5$, R$_6$, R$_7$, R$_8$ and R$_9$ may together form an optionally substituted carbocyclic or heterocyclic group, such as an optionally substituted aromatic or heteroaromatic group and/or an optionally substituted cycloalkyl or hetero cycloalkyl group;

or a pharmaceutically acceptable salt or solvate thereof or a tautomer thereof, for use in the treatment of hyperphenyl-alaninemia (HPA), in particular phenylketonuria (PKU).

These compounds defined above are particularly of use in the treatment of MHP and mild PKU but also patients with classic PKU who retain ≥10% of wild-type PAH activity. Different misfolding mutations can result in PAH having more or less residual enzymatic activity. The Examples herein describe a suitable assay of PAH activity.

Preferred substituents of the optionally substituted C$_{2-6}$ alkenyl, C$_1$-C$_6$ alkyl, aminoalkyl, alkoxy, thiol or heteroalkyl group include one or more, which may be the same or different, of the following: halogen, CN, OH, NH$_2$, NO$_2$, SH, O, optionally substituted C$_1$-C$_3$ alkyl, optionally substituted C$_2$-C$_3$-alkenyl, optionally substituted C$_1$-C$_3$ alkoxy, optionally substituted C$_1$-C$_3$ thiol, optionally substituted C$_1$-C$_3$ aminoalkyl, optionally substituted C$_1$-C$_3$ heteroalkyl, wherein heteroatoms are selected from N, O or S and a cyclic group which may be aromatic or aliphatic and may be a 4, 5 or 6 membered ring, optionally containing one or more heteroatoms selected from O, N and S, said cyclic group being optionally substituted.

One or more of R$_1$-R$_9$ may comprise cyclic aliphatic groups (e.g. cycloalkyl and cycloheteroalkyl) or aromatic groups. These cyclic groups are optionally substituted. Preferred substituents include one or more, which may be the same or different, of the following: halogen, CN, OH, NH$_2$, NO$_2$, SH, O optionally substituted C$_1$-C$_3$ alkyl, optionally substituted C$_2$-C$_3$ alkenyl, optionally substituted C$_1$-C$_3$ alkoxy, optionally substituted C$_1$-C$_3$ thiol, optionally substituted C$_1$-C$_3$ aminoalkyl, and optionally substituted C$_1$-C$_3$ heteroalkyl.

Preferred cyclic moieties include phenyl, piperidinyl, piperazinyl, oxopiperidinyl, pyrrolidinyl, imidazolyl, pyridyl, pyrazinyl, pyrimidinyl, oxazolyl, isoxazolyl, morpholinyl, indolyl, thienyl, furyl and thiomorpholinyl.

Preferred substituents of the optionally substituted C$_{2-3}$ alkenyl, C$_{1-3}$ alkyl, aminoalkyl, alkoxy, thiol or heteroalkyl group include halogen, NH$_2$, OH, SH, O, CN and NO$_2$.

Unless otherwise indicated, alkyl, alkenyl, alkoxy, aminoalkyl, thiol or heteroalkyl groups may be linear, branched or cyclic. For example, C$_1$-C$_6$ thiol includes groups wherein the C$_1$-C$_6$ group is linear, branched or cyclic (either aliphatic or aromatic).

Where compounds of the invention are chiral, they may be present as pure enantiomers or in racemic or other mixtures.

Unless otherwise indicated, preferred halogens are F or Cl. Multiple substitutions are contemplated, thus providing, for example, partial or full fluorination of a carbon atom.

Groups comprising heteroatoms may comprise more than one heteroatom, which may be the same or different. Likewise, moieties which are optionally substituted may have multiple substitutions which may be the same or different.

An aminoalkyl group may be a secondary or tertiary amine and each alkyl may be substituted as defined herein.

Preferably, R$_1$, R$_2$ and R$_3$, which may be the same or different, are selected from the group consisting of H, NH$_2$, OH, CN, NO$_2$, SH, optionally substituted C$_1$-C$_6$ alkyl or C$_2$-C$_6$ alkenyl, optionally substituted C$_1$-C$_6$ heteroalkyl wherein the heteroatoms are one or more N, O or S, optionally substituted C$_1$-C$_6$ thiol, optionally oxidized to —S(O)— or —S(O)$_2$—, optionally substituted C$_1$-C$_6$ aminoalkyl, optionally substituted C$_1$-C$_6$ alkoxy, (Y)$_p$CO(Z)$_q$R$_A$ and an aromatic group, optionally containing one or more heteroatoms selected from O, N and S, said aromatic group being optionally substituted, wherein Y and Z are independently selected from O and N(R$_B$), p and q are independently 0 or 1, R$_A$ is selected from the group consisting of H, optionally substituted C$_1$-C$_6$ alkyl or C$_2$-C$_6$alkenyl, and optionally substituted C$_1$-C$_6$ heteroalkyl wherein the heteroatoms are one or more N, O or S, and R$_B$ is selected from H and C$_1$-C$_3$ alkyl or cycloalkyl.

More preferably, R$_1$, R$_2$ and R$_3$, which may be the same or different, are selected from SH, C$_1$-C$_6$ heteroalkyl (e.g. —SMe), optionally fluorine-substituted C$_1$-C$_6$ alkyl, NH$_2$ and OH; preferably CF$_3$, NH$_2$ and OH; more preferably NH$_2$ and OH.

In particularly preferred embodiments one or more of R$_1$, R$_2$ and R$_3$ is NH$_2$, for example R$_2$ and R$_3$ or R$_1$ and R$_2$ are each NH$_2$.

If R$_1$ is NH$_2$ then R$_3$ may conveniently be H or OH, or vice versa.

It is preferred that at least two of R$_1$, R$_2$ and R$_3$ are NH$_2$ or OH, with NH$_2$ being particularly preferred. If two of R$_1$, R$_2$ and R$_3$ are NH$_2$, the other R$_1$, R$_2$ or R$_3$ group may be any other substituent listed above, such as H, C$_1$-C$_6$ alkyl (e.g. methyl or ethyl), halogen, NH$_2$ or OH.

Preferably, R$_2$ is NH$_2$ and one or both of R$_1$ and R$_3$ is also NH$_2$, with the other being H.

For compounds of formula (IIa) or (IIb), R$_2$ is preferably NH$_2$ and R$_1$ or R$_3$ is preferably OH.

Two or possibly three of R$_1$, R$_2$ and R$_3$ are each individually preferably NR$_A$R$_B$, where R$_A$ and R$_B$ may form a ring together and are as defined above, the third is preferably hydrogen.

R$_4$ is preferably H or fused to R$_1$ or R$_3$. R$_4$' is preferably H. R$_4$ and R$_4$' may together form =O or =S, =O being preferred.

Preferably R$_5$, R$_6$, R$_7$, R$_8$ and R$_9$ do not all represent H, preferably 2 or 3 of R$_5$, R$_6$, R$_7$ and R$_8$ do not represent H.

In preferred embodiments, 1, 2 or 3, preferably 2 or 3 of $R_5$, $R_6$, $R_7$, $R_8$ and $R_9$ are $C_1$-$C_3$ alkoxy, most preferably methoxy. In other preferred embodiments two of $R_5$, $R_6$, $R_7$, $R_8$ and $R_9$ form 5- or 6-membered rings, preferably with 1 or 2 heteroatoms, most preferably with 2 oxygen atoms such as —O—CH$_2$—CH$_2$—O— or —O—CH$_2$—O—. Halogens, in particular F or Cl, are also preferred at these positions (one or more of $R_5$, $R_6$, $R_7$, $R_8$ and $R_9$), either as individual halogen atoms or as substituents on a carbon atom, e.g. to provide a partially or fully fluorinated carbon atom.

Preferably, $R_5$, $R_6$, $R_7$, $R_8$ and $R_9$, which may be the same or different, are selected from methoxy, SCH$_3$, OH, Cl, F, or methyl, or two of $R_5$, $R_6$, $R_7$, $R_8$ and $R_9$ together form —O—CH$_2$—CH$_2$—O—, —O—CH$_2$—O— or phenyl.

More preferably, $R_5$, $R_6$, $R_7$, $R_8$ and $R_9$, which may be the same or different, are selected from methoxy and Cl, or two of $R_5$, $R_6$, $R_7$, $R_8$ and $R_9$ together form —O—CH$_2$—O— or phenyl, preferably —O—CH$_2$—O—.

$X_1$ is preferably N.

$X_2$ is preferably $NR_{10}$, with NH being particularly preferred.

$X_3$ is preferably —C(=O)—.

Preferably, $X_1$ is N, $X_2$ is —NH—, and $X_3$ is —C(=O)—.

In certain preferred embodiments the compounds of formula I do not have a strong inhibitory effect on dihydrofolate reductase (DHFR) e.g. they inhibit (human) DHFR less than trimethoprim (TMP) (c53 in FIG. 4), preferably exhibiting at least 20% or 50% or 70% or 90% less inhibition. Preferably, the compounds of formula I have no, or essentially no, inhibitory effect on DHFR. Essentially no inhibitory effect implies not measurable and/or of no physiological significance. This reduced inhibition may be provided by modification of the pyrimidine ring of TMP, thus $X_1$ may preferably be C and/or one or both of $R_1$ or $R_3$ is preferably other than H or NH$_2$, more preferably aminoalkyl, alkyl, or thiol e.g. N(CH$_3$)$_2$ or, $C_{1-3}$ alkyl or $C_{1-3}$ thiol, optionally oxidized to —S(O)— or —S(O)$_2$—.

Some preferred compounds for use in the treatments of the invention are shown below, for example in which hydrogen is found in certain positions; all other atoms and substituents and preferred substituents are as defined herein.

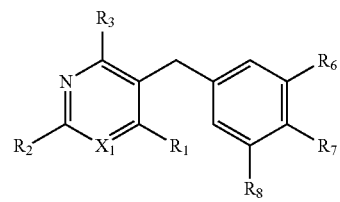

Compounds of formula III

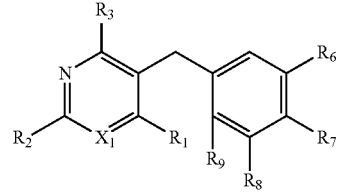

Compounds of formula IV

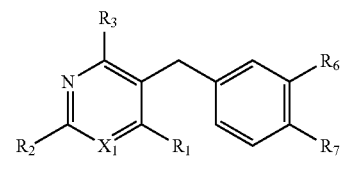

Compounds of formula V

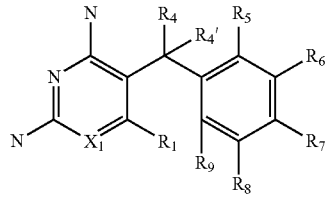

Compounds of formula VI

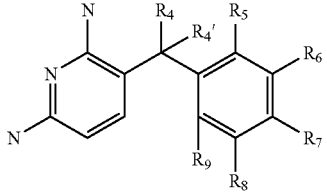

Compounds of formula VII

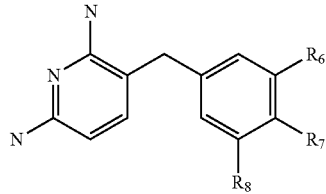

Compounds of formula VIII

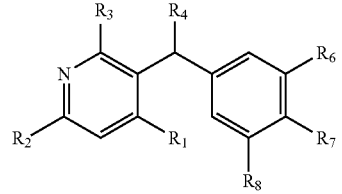

Compounds of formula IX

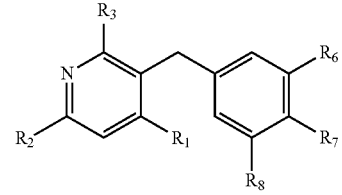

Compounds of formula X

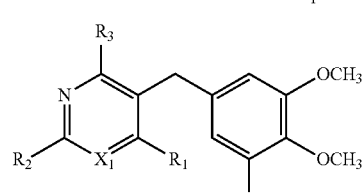

Compounds of formula XI

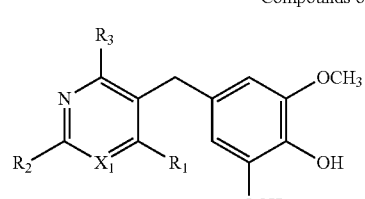

Compounds of formula XIIa

Compounds of formula XIIb

Compounds of formula XIIc

Compounds of formula XIId

Compounds of formula XIII

Compounds of formula XIV

Compounds of formula XV

Compounds of formula XVI

Compounds of formula XVII

Compounds of formula XVIII

Compounds of formula XIXa

Compounds of formula XIXb

Compounds of formula XIXc

Compounds of formula XX

Compounds of formula XXIa

Compounds of formula XXIb

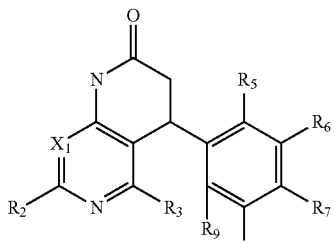

Compounds of formula XXII

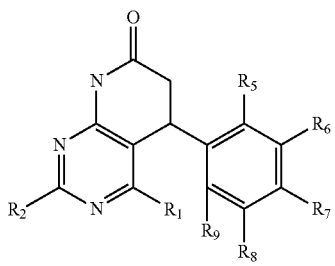

Compound of formula XXII are particularly preferred, with the substituents $R_1$, $R_2$, $R_5$, $R_6$, $R_7$, $R_8$ and $R_9$ defined as above.

Preferably the uses and methods of the present invention do not employ TMP.

Some preferred compounds are disclosed in the Examples and Figures. Particularly preferred compounds of the invention are compounds 53; 53.4; 53.10; 53.14; 53.17; 53.20; 53.22; 53.35; 53.40 and 53.41.

HPA and PKU treatable according to the present invention are caused by reduced PAH activity and the compounds of formula (I) act as pharmacological chaperones to mutant forms of PAH, in particular those forms with ≥10% residual activity, increasing their stability and therefore their catalytic activity, i.e. ability to convert L-Phe to L-Tyr. Different mutant forms of PAH are known in the art and mutants which may have their stability improved according to the present invention include the following human mutant forms I65T, R68S, R252W and R261Q, in particular I65T, R68S and R261Q (mutation defined by native amino acid using the single letter code, followed by location and then by the substituting amino acid). Mutant R252W may require co-administration with a $BH_4$ in order to achieve an increase in PAH levels.

The Examples provide suitable in vitro methods using wild-type or mutant forms of PAH which may be used to confirm efficacy, estimate dosage etc. of a compound of formula I.

Treatment includes prophylaxis in that the patient may not have detectable symptoms of HPA or PKU; nevertheless, most patients treated in accordance with the present invention will have been diagnosed with HPA or PKU or suspected of having HPA or PKU. Methods of diagnosis of these conditions are known in the art. Treatment and prophylaxis may not be absolute but will result in a measurable improvement in one or more parameters (e.g. symptom or biochemical marker) associated with HPA or PKU, or in the case of prophylaxis, prevention or reduction of the otherwise expected development of traits of HPA/PKU.

Alternatively viewed, the present invention provides a method of treating a subject having or suspected of having HPA, in particular PKU, comprising administering to the subject an effective amount of a compound of formula I as defined above or a pharmaceutically acceptable salt, solvate or tautomer thereof.

Unless otherwise clear from the context, reference herein to compounds of formula I can be taken also as reference to compounds of formulae II to XXII.

Likewise, the present invention provides a method of treating HPA, in particular PKU, in a subject by administering to a subject in need thereof a compound of formula I as defined above or a pharmaceutically acceptable salt, solvate or tautomer thereof. Alternatively viewed the present invention provides a method of treating HPA, in particular PKU, in a subject by administering thereto an effective amount of a compound of formula I as defined above or a pharmaceutically acceptable salt, solvate or tautomer thereof.

In a further aspect, the present invention provides a compound of formula I as defined above or a pharmaceutically acceptable salt, solvate or tautomer thereof for use in increasing the stability of PAH. Also provided is the use, which may be in vitro or in vivo, of a compound of formula I as defined above or a salt, solvate or tautomer thereof to increase the stability of PAH. Alternatively viewed, the present invention provides a method of increasing the stability of PAH comprising contacting with or administering a compound of formula I as defined above or a pharmaceutically acceptable salt, solvate or tautomer thereof. An increase in PAH stability typically leads to an increase in cellular PAH levels and/or in PAH activity.

The compound is administered according to a therapeutically effective dosage regimen which may require multiple administrations, e.g. 2 to 100, typically at least 10 or 20 doses, such doses may conveniently be administered daily. Typical daily doses will be between 1 and 20 mg/kg/day. A therapeutically effective dosage regimen will be one to effect treatment or prophylaxis, as defined above.

Effective amounts and effective dosage regimens are able to cause measurable and physiologically relevant increases in PAH activity in the subject, e.g. an observed improvement in Phe metabolism.

The present invention further provides use of a compound of formula I as defined above or a pharmaceutically acceptable salt, solvate or tautomer thereof in the manufacture of a medicament for the treatment of HPA, in particular PKU.

The compounds of formula I may be formulated for administration in any convenient way, typically in a composition with a physiologically acceptable carrier, diluent or excipient.

The compounds and compositions may be administered to the subject in any convenient form or by any convenient means, e.g. by topical, oral, parenteral, enteral, parenteral routes or by inhalation. Oral or parenteral routes are preferred.

The skilled man will be able to formulate the molecules of the invention into pharmaceutical compositions that are adapted for these routes of administration according to any of the conventional methods known in the art and widely described in the literature.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), ointments, soft and hard gelatine capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof.

The compositions may additionally include lubricating agents, wetting agents, emulsifying agents, suspending agents, preserving agents, sweetening agents, flavouring agents, and the like.

Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 18th ed., Mack Publishing Co. The solutions can contain preservatives, antimicrobial agents, buffers and antioxidants conventionally used for parenteral solutions, excipients and other additives which are compatible with the active compounds and which will not interfere with the manufacture, storage or use of products.

Individual doses may contain 0.01 to 40 mg/kg, e.g. 0.02 to 2 mg/kg.

The exact dose will depend on the purpose of the treatment, and will be ascertainable by one skilled in the art using known techniques. As is known in the art, adjustments for systemic versus localized delivery, age body weight, general health, sex, diet, time of administration drug interaction and the severity of the condition may be necessary, and will be ascertainable with routine experimentation by those skilled in the art.

The subject will typically be a human subject but may be another animal, e.g. a livestock or domestic animal; and thus the invention has utility in human and veterinary therapy.

The uses, treatments and compositions defined herein may also include the use of a second active agent, e.g. a second active agent for treating HPA or PKU. Preferred combination treatments include co-administration of a compound which acts as a cofactor of PAH, i.e. tetrahydrobiopterin ($BH_4$) or analogues or precursors thereof, e.g. the commercially available product Kuvan® which may preferably be administered with ascorbic acid.

The present invention also provides a composition comprising a compound of formula I or a pharmaceutically acceptable salt or solvate thereof and a further agent effective in the treatment of HPA, in particular PKU.

The present invention also provides a pharmaceutical pack comprising, not in admixture but for simultaneous or sequential administration, a compound of formula I or a pharmaceutically acceptable salt or solvate thereof and a further agent effective in the treatment of HPA, in particular PKU.

"Sequential" does not imply any particular order or proximity to the administration (temporally or spatially), simply that the two agents are part of a combination therapy where they are not simultaneously administered.

Said packs or compositions preferably comprise $BH_4$ or an analogue or precursor thereof, e.g. Kuvan®.

Nevertheless, preferred treatments according to the invention do not require a second active and in particular do not require $BH_4$ or an analogue or precursor thereof.

The present invention is described in the following non-limiting examples and figures:

FIG. 1. Effect of compounds 1-7, compounds III and IV (from Pey et al., 2008) and of $BH_2$ on PAH immunoreactive protein level and on PAH activity determined on lysates of HEK293 cells permanently expressing human wild-type PAH. (A) The cells were grown for 24 h in normal medium and then 0.04 mg/ml (average 116.7 µM) of the separated compounds (with 1% DMSO) was added. The controls contained 1% DMSO. After 8 h further incubation at these conditions the cells were harvested and PAH protein was determined by Western blot and activity measured in clarified lysates. (B) PAH activity when the compounds were added together with the $BH_4$ precursor $BH_2$ (200 µM). $BH_2$ (200 µM) alone, at the same conditions, had a stimulating effect of 24.8% on PAH protein and 21.7% on PAH activity.

FIGS. 2A-2G. Effect of Compound 53 and $BH_2$ on the immunoreactive hPAH protein level (FIGS. 2A-2D) and PAH activity (FIGS. 2E-2H) of HEK293 EBNA cells transiently expressing the indicated PKU mutants. A concentration of 200 µM for Compound 53 and $BH_2$ was used and FIGS. 2A-2D show as well the original blotting membranes. (*) Significant differences with respect to the mutant-1% DMSO control, $p<0.05$.

Figure 3:
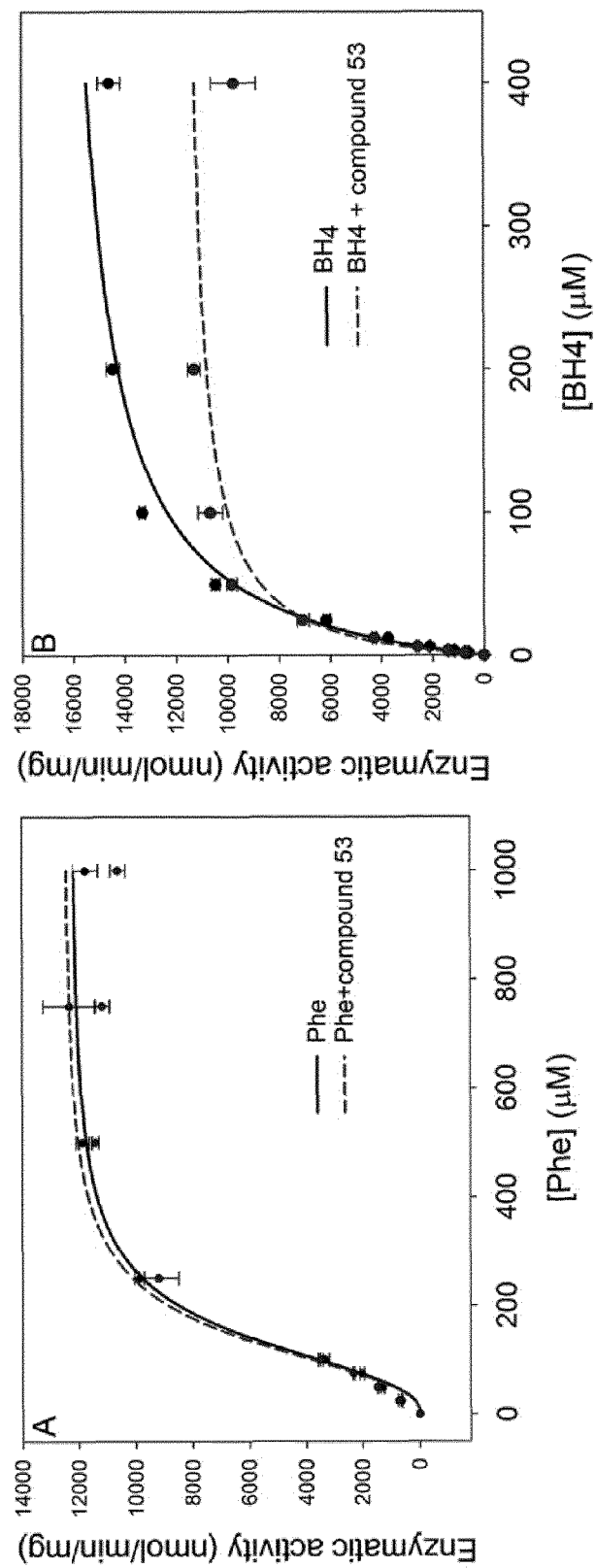
Figure 3:
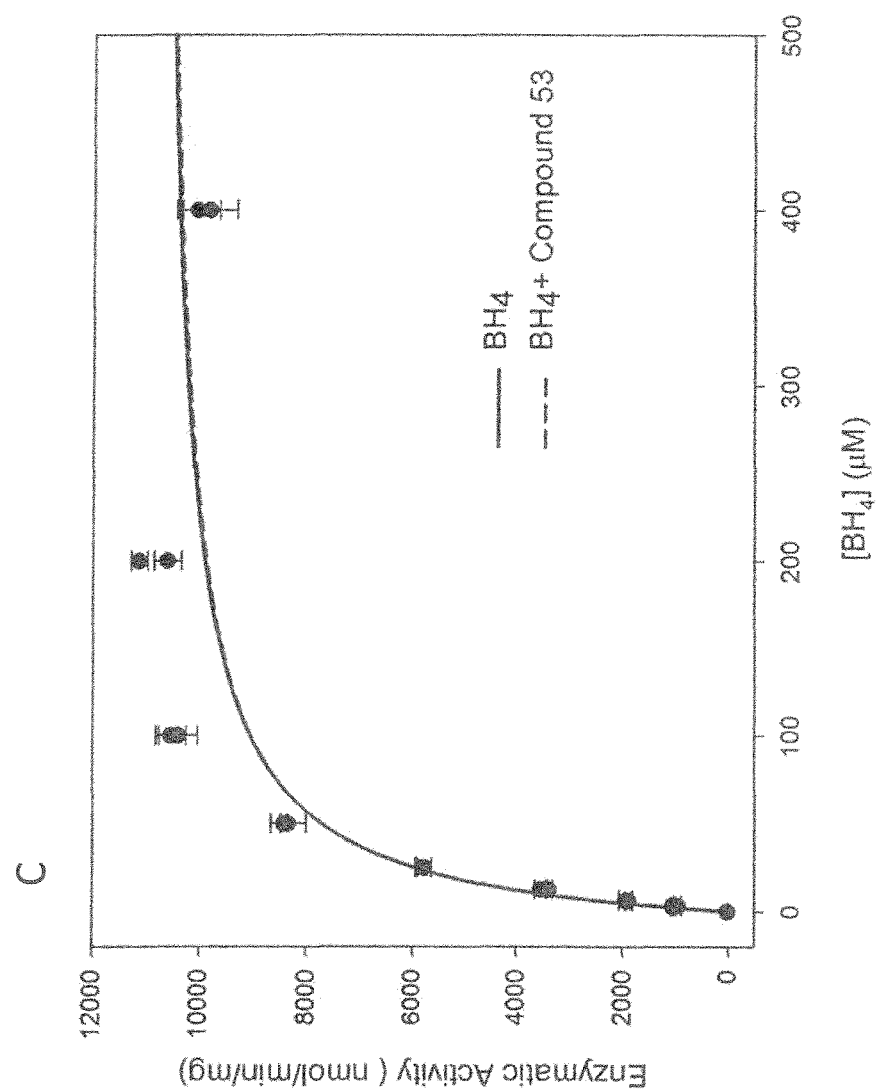

FIG. 3. The effect of Compound 53 on the activity of hPAH. Effect of Compound 53 on (A) the Phe dependent specific activity of full-length tetrameric wild-type hPAH, assayed at 100 µM $BH_4$, (B) the $BH_4$-dependent activity of full-length hPAH, assayed with 1 mM L-Phe, and (C) the $BH_4$-dependent activity of truncated dimeric hPAH ΔN102/ΔC24, assayed with 1 mM L-Phe. (D) A summary of the calculated steady state enzyme-kinetic parameters. Values are expressed as the average of three independent experiments±SD. The concentration of Compound 53 in the assays was 137.8 µM and 2% DMSO. **Significant Differences with respect to control, $p<0.01$.

Figure 4:
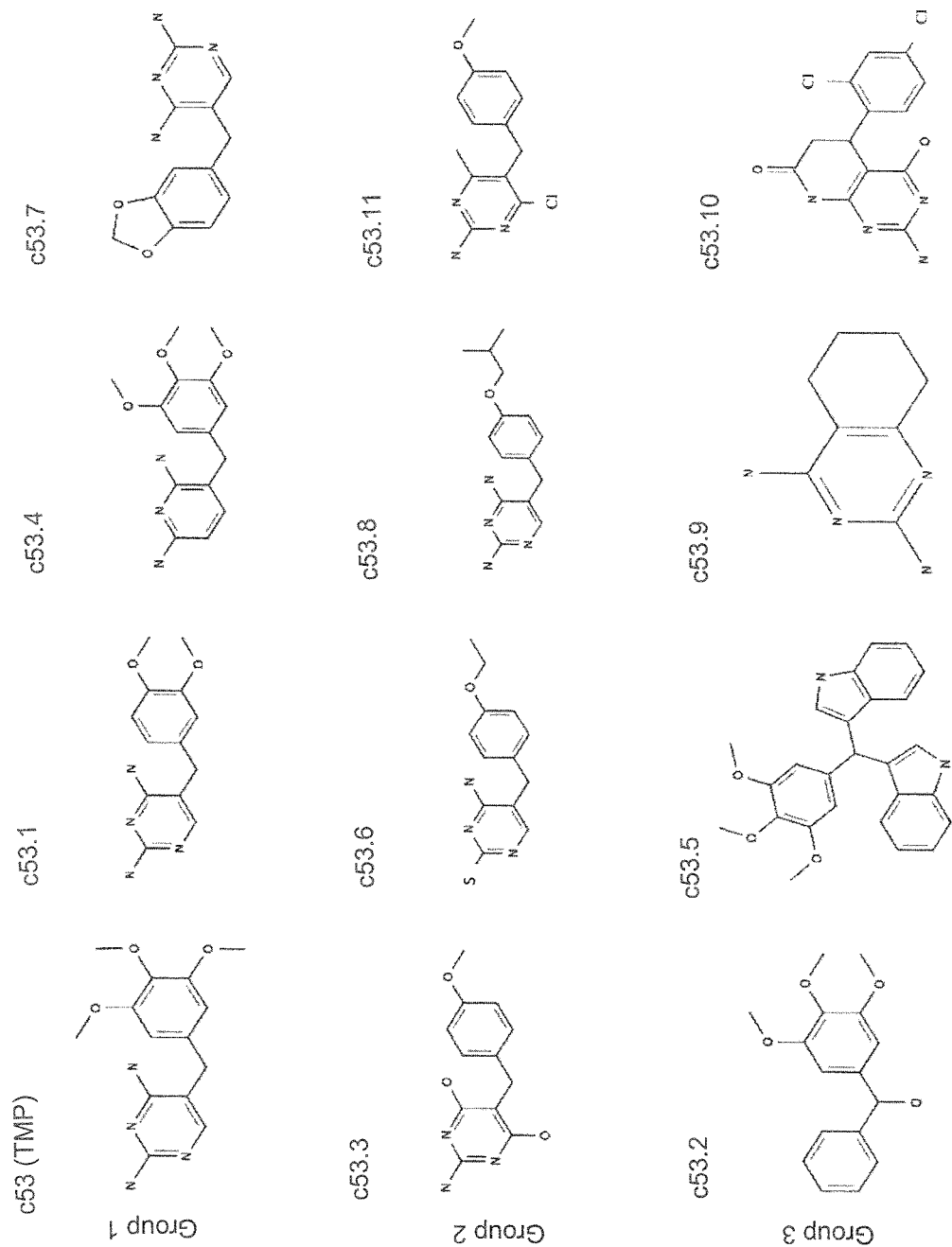

FIG. 4. Analogues of Compound 53 identified through similarity search of commercially available compounds. 11 selected compound analogues of Compound 53 grouped based on the number of atom substitutions: group 1 analogues (≤3 atom substitutions) are shown in row 1; group 2 analogues (>3 atom substitutions) in row 2; group 3 (different scaffold) in row 3.

Figure 5:
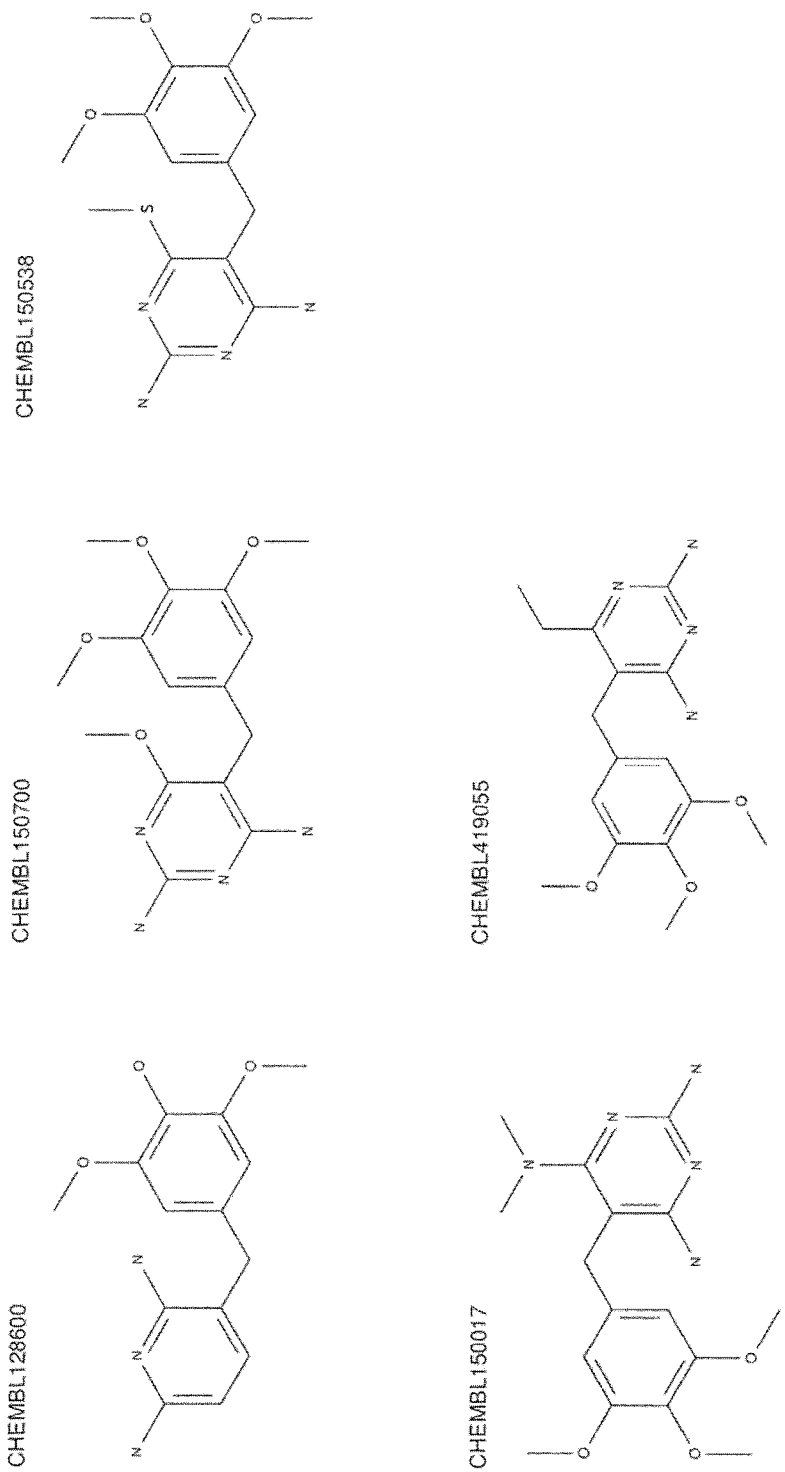

FIG. 5. Selected compounds from the ChEMBL database with the same scaffold as Compound 53, but with substitutions notably on the pyrimidine ring, yielding reduced affinity for DHFR.

Figure 6:
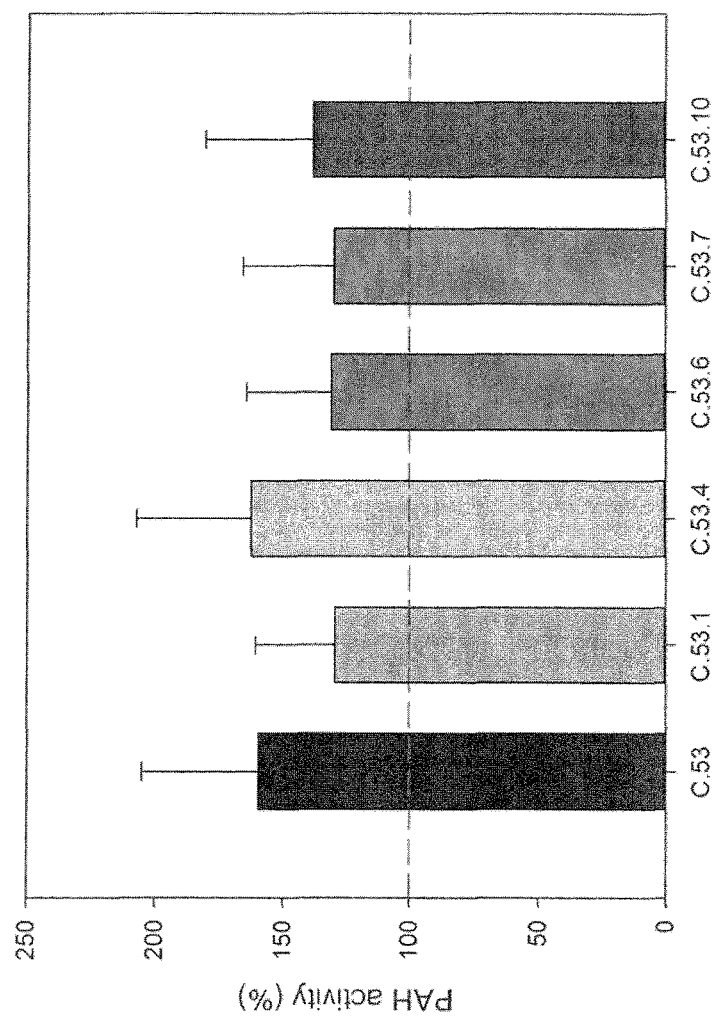

FIG. 6. Effect of Compound 53 derivatives on PAH activity in lysates from HEK293 cells permanently expressing human wild-type PAH, cultured in the presence of an average compound concentration of 144.9 µM, with 1% DMSO. The dashed line represents the normalized activity of the control (1% DMSO), also used as reference for the activity values of the compounds.

Figure 7:
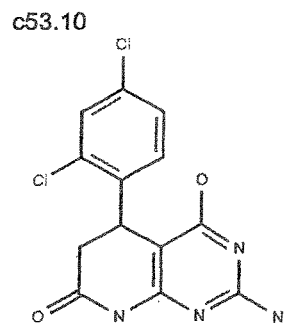
Figure 7:
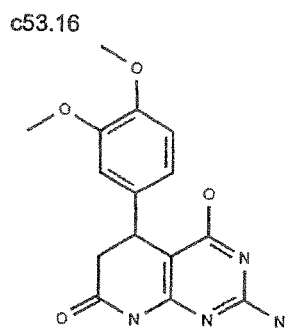
Figure 7:
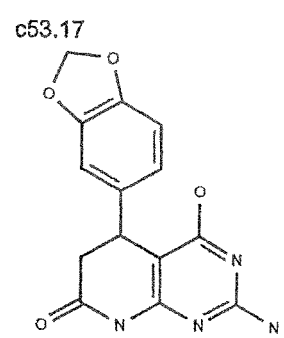
Figure 7:
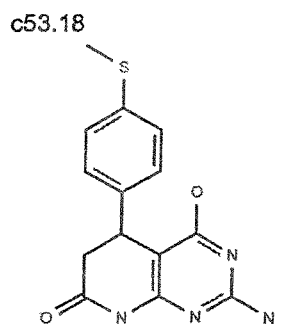
Figure 7:
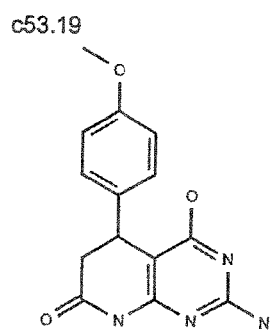
Figure 7:
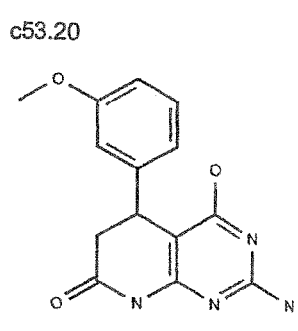
Figure 7:
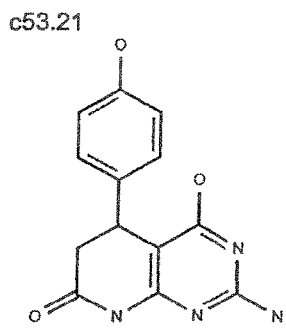
Figure 7:
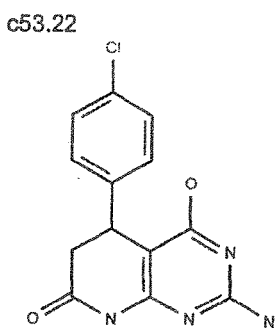

FIG. 7. A selection of further compounds (analogues of Compound 53.10) for use according to the present invention, chaperone activity has been confirmed by DSF testing.

Figure 8:
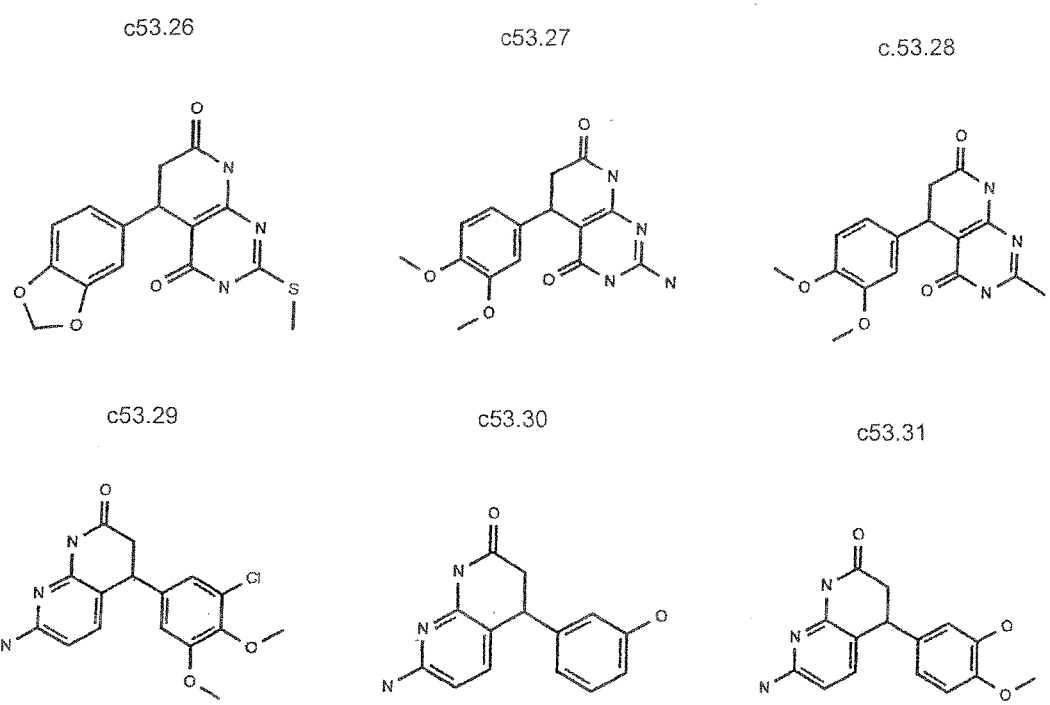

FIG. 8. A selection of further compounds (analogues of Compound 53.10) for use according to the present invention.

Figure 9:
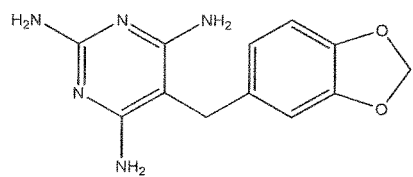
Figure 9:
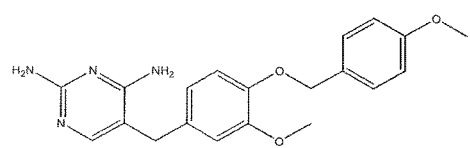

FIG. 9. A selection of further compounds (analogues of Compound 53) for use according to the present invention.

Figure 10:
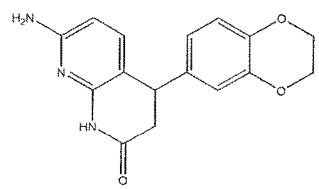
Figure 10:
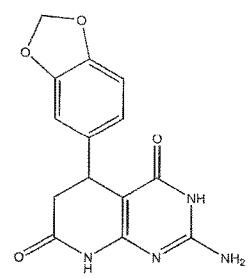
Figure 10:
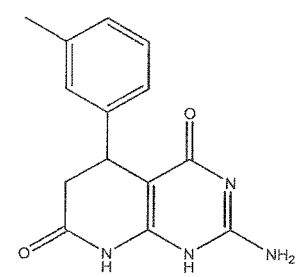
Figure 10:
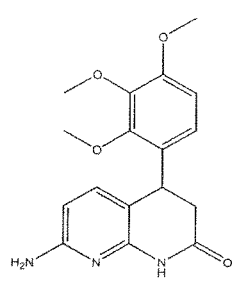
Figure 10:
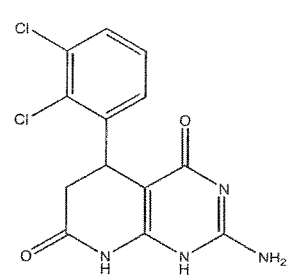
Figure 10:
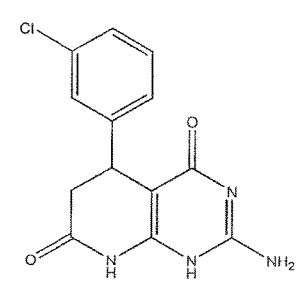
Figure 10:
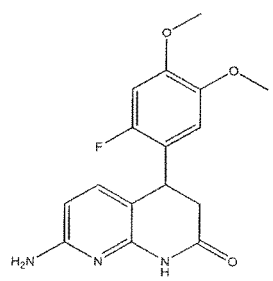
Figure 10:
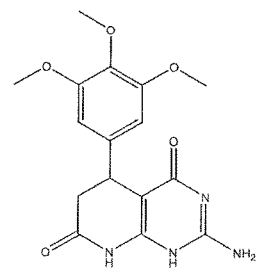
Figure 10:
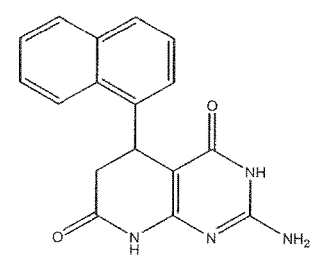

FIG. 10. A selection of further compounds (analogues of Compound 53.10) for use according to the present invention.

EXAMPLES

Example 1

Materials And Methods
Materials
Compounds

Compounds were ordered from TimTec and Sigma Aldrich (purity >90% for the different batches), prepared at concentrations of 4 mg/mL in 100% DMSO. Compounds III and IV from Pey et al., 2008, supra, were obtained from Maybridge (Maybridge Ltd., UK)

Enzymes

Tetrameric full length wild-type (WT) human PAH (hPAH) and truncated ΔN102/ΔC24-hPAH corresponding to a dimeric form containing the catalytic domain of known crystal structure were recombinantly expressed in E. coli fused to maltose-binding protein and purified by amylose-affinity chromatography and further cleaved and isolated to homogeneity essentially as described [Martinez, A., et al., Biochem. J., 1995. 306: p. 589-597]. Protein concentration was measured in a NanoDrop spectrophotometer (Thermo Scientific) using the absorbance at 280 nm and the theoretical molar extinction coefficient of 49780 $M^{-1}$ $cm^{-1}$ for WT-PAH and 46675 $M^{-1}$ $cm^{-1}$ for ΔN102/ΔC24-hPAH.

Assay of PAH Activity

PAH activity on isolated recombinant enzymes was measured at 37° C. for 1 min with quantification of L-Tyr formed by HPLC with fluorimetric detection, essentially as described [Martinez et al. supra] with the indicated concentrations of the compounds. In order to better eliminate the PAH inhibitors, we further adapted the assay: reaction mixtures containing 0.25 μg of hPAH, 100 mM NaHepes pH 7.0, 20 mM NaCl, 0.04 mg/ml catalase, 50 μM ferrous ammonium sulphate, 1 mM L-Phe, 0.05% bovine albumin serum, 2% DMSO and 0.04 mg/ml compound were dispensed in a 96-well PCR plates (Roche) and incubated for 40 min at 42° C. After an equilibration of the plate at 37° C. for 3 min the reaction was initiated by adding 75 μM $BH_4$ (Schircks Laboratories, Jona, Switzerland) in 5 mM DTT and stopped after 1 min by adding 50 μl of 2% (v/v) acetic acid in ethanol (all concentrations referred to a final reaction volume of 50 μl) prior to determination of L-Tyr produced by HPLC with fluorimetric detection ($\gamma_{excitation}$=274 nm; $\gamma_{emission}$=304 nm). Controls with 2% DMSO without compound were routinely assayed as references for data processing. A BRAVO automated liquid handling platform was used in these assays.

The steady-state kinetic parameters were estimated with 0.25 μg hPAH (0.965 μM subunit), 1 mM L-Phe and different $BH_4$ concentrations in the range 0-400 μM, and with 100 μM $BH_4$ and L-Phe (0-1 mM). The saturation curves were fitted to hyperbolic (for $BH_4$) or sigmoidal (for L-Phe) kinetic models with SigmaPlot v. 9.0. (SPSS). Kinetic parameters are presented as mean±SEM obtained from nonlinear regression analysis.

A similar assay was used to measure PAH activity in cells lysates using 1 mM L-Phe and 200 μM $BH_4$ with 10 min reactions and about 20-90 μg of total protein. Free amino acids and contaminants of low molecular weight were previously removed from the extracts using Zebra Desalt Spin columns (Pierce Biotechnology). Under these conditions, PAH activity was linear to the amount of protein in the extracts.

Expression of WT and Mutant PAH in Eukaryotic Cells

Human embryonic kidney cells (HEK293; Life Technologies™) permanently expressing WT-hPAH, prepared with the Flp-In system (Life Technologies™) were kindly provided by Per Knappskog, Haukeland University Hospital. About 1 million cells were grown in DMEM medium containing 4.5 g/l glucose, 10% (v/v) fetal calf serum, 0.25 mg/ml gentamycine, 2 mM L-glutamine and 50 μg/ml hygromycin B, and after 24 h medium was changed and the test compounds were added at a concentration of 0.02 mg/ml (1% DMSO). Eight hours later, the cells were harvested, and the pellets frozen in dry ice and stored at −80° C. Control experiments revealed no significant effects of 1% DMSO either on cell growth and survival or on PAH activity and immunoreactivity (data not shown). To prepare the cell extracts, the frozen cell pellets were thawed in TBS (+protease inhibitor) buffer and cells were homogenized with 0.1% TX-100, incubated 15 minutes at 4° C. and extracts were clarified by centrifugation 20000 g for 15 min at 4° C. Protein concentrations were normalized using a Direct Detect Spectrometer (Merck Millipore).

The 7 selected compounds as well as the first generation pharmacological chaperones (Compounds III and IV) were further analyzed in the presence and absence of $BH_2$ (200 μM), added as precursor of $BH_4$, to account for additive effects. A higher concentration of compound was also used 0.04 mg/ml (average of 116.7 μM) at otherwise same experimental conditions.

For transient expression of WT and mutant PAH, HEK293 EBNA (Epstein-Barr virus) cells, with low endogenous PAH expression, were grown as above. Cells were grown for 19 h, when they were transfected transiently transfected with 1 pg of pcDNA3-PAH vector (WT or mutant PAH constructs R261Q, R252W, I65T and R68S) using the Lipofectamine system (Life Technologies™) as described by the manufacturer. Compound 53, with and without $BH_2$ (200 μM) was added after 5 h of transfection at 200 μM concentration in 1% DMSO, and further incubated for 24 h, at which time the cells were harvested and stored at −80° C. In all cases a parallel negative control with only 1% DMSO was included. Cell lysates were prepared as indicated above.

Western Blot Analyses

Western blot analyses were performed on either cell extracts from permanently expressing or transiently transfected HEK293 cell lysates after SDS-PAGE (10% acrylamide) with 5-10 μg total protein in each lane. Proteins were transferred into a PVDF membrane and subsequently blocked and incubated with a polyclonal mouse anti-human PAH (PH8; Merck Millipore) at 1 μg/ml, neomycin phosphotransferase II (Merck Millipore #06-747) and GAPDH (Abcam, #ab9485) as primary antibodies. Neomycin phosphotransferase II was used as a marker of the plasmid transfection efficiency, and GAPDH was used as loading controls. Goat anti-mouse and goat anti-rabbit HRP conjugate (Bio-Rad) were used as secondary antibodies. Lastly, membranes were developed by chemiluminescence (ECL; Amersham), and immunoquantification in a Fluor-S Multi-lmager (Bio-Rad) using ImageLab v.5.1 software.

Derivatization/Selection of Related Structures to Compound 53

Similarity search for Compound 53 analogues was performed using the R-package ChemInf and OpenBabel [O'Boyle, N. M., et al., J Cheminform, 2011. 3: p. 33] over a selection of small molecule libraries of purchasable compounds obtained from the chemical vendors Vitas-Lab, Sigma Aldrich, Otava and MolPort. All compounds showing a Tanimoto coefficient of >0.5. towards compound 53 were selected for manual inspections.

Differential Scanning Fluorimetry (DSF)

DSF was used to monitor the thermal denaturation of recombinant WT-hPAH protein in the presence of the fluorescent dye SYPRO Orange (Sigma-Aldrich). The experiments were carried out in a LightCycler 480 Real-Time PCR (RT-PCR) instrument (Roche Applied Science, Indianapolis, Ind.). In each well 49 µl of a hPAH protein solution containing 0.1 mg/ml (1.93 µM subunit) in 20 mM NaHepes pH 7.0, 200 mM NaCl and 5×SYPRO Orange, were dispensed with the help of a multichannel pipette. Next, in a BRAVO automated liquid handling platform (Agilent Technologies, Santa Clara, Calif.) 1 µl of each test compound was added to a final volume of 50 µl/well, with final concentrations of 4% DMSO and 0.04 mg/ml compound. Plates were incubated at room temperature (RT) for 30 min before loading them into the LightCycler and starting the data acquisition. The thermal denaturation was monitored by following the expected increase in fluorescence intensity of the extrinsic probe SYPRO Orange (instrument filter settings: $\lambda_{exc}$=465 nm; $\lambda_{em}$=610 nm) as a consequence of the unfolding/denaturation of the protein. Melting curves were registered from 20 to 95° C. at a scan rate of 2.4 ° C./min and the experimental data obtained allowed the extraction of values of $T_m$ (midpoint melting temperature) by fitting, smoothing, normalization and analysis of the aforementioned unfolding curves using in-house software. $T_m$ represents the temperature at which the fraction of unfolded (or folded) protein is 50% and it is calculated as the intersection between denaturation curve and fraction of unfolding $_xU$=0.5. Control experiments with 4% DMSO were performed in the same way.

The $T_m$-values for hPAH in the presence of each compound was compared to the value for the control without compound but with 4% DMSO, and the shifts in Tm ($\Delta T_m$) were calculated. $\Delta T_m$ (=$T_m$ Compound−$T_m$ DMSO control).

Results

Expression Studies in HEK293 Cells Permanently Expressing hPAH

We analyzed the effect of 20 compounds on the cell growth of HEK293 expressing hPAH at 0.02 mg/ml, as well as on the immunoquantified levels of hPAH protein and activity. Many of the compounds provoked the detachment of the cells and we thus only selected 7 evidently non-toxic compounds with the best profiles to be further analyzed at a higher concentration, 0.04 mg/ml. In addition, we also examined if the compounds provided additive or synergetic effects with $BH_4$. We used $BH_2$ as precursor of $BH_4$ since the addition of $BH_4$ directly to the cellular medium is toxic, while $BH_2$ is taken up and intracellularly converted to $BH_4$.

The compounds were analyzed at an average concentration of 116.7 µM and $BH_2$ at 200 µM. Control experiments with 1% DMSO were also performed. As observed in FIG. 1A, one of the compounds, Compound 53, had a very large stimulating effect on PAH protein and activity, especially the latter. This effect was larger than that of compounds III and IV, first generation pharmacological chaperones from Pey et al., 2008 (supra). Furthermore, the effect of compound B with $BH_2$ was additive (FIG. 1B). Finally, this compound at a concentration of 68.9 µM did not have large effect on TH and TPH2 activity respect to 2% DMSO controls.

From this point we decided to focus on Compound 53 as the best hit for further characterizations and hit optimization.

Expression Studies in HEK293 Cells Transiently Expressing PKU Mutants

We studied the transient expression of the PKU mutants I65T-, R68S-, R252W- and R261Q-PAH in cells for 24 hours in the absence or presence of 200 µM of compound 53, without and with 200 µM $BH_2$. These 4 PKU mutations represent 4 different phenotypic groups in PKU patients, and allele recurrence: R68S is a mild mutation (frequency>2% of the alleles), I65T is mild-moderate (frequency=3.9% of the alleles), R261Q is highly variable (mild-moderate-severe) and very frequent (9.2% of alleles), and R252W is a severe mutation (frequency=2.5% of the alleles). Cells were harvested, and steady-state PAH immunoreactive protein at 51 kDa, corrected for loading (GAPDH; 38 kDa) and expression controls (Neo;30 kDa) and PAH activity were measured in soluble cell extracts (FIGS. 2A-2G).

Figures 2A, 2B:
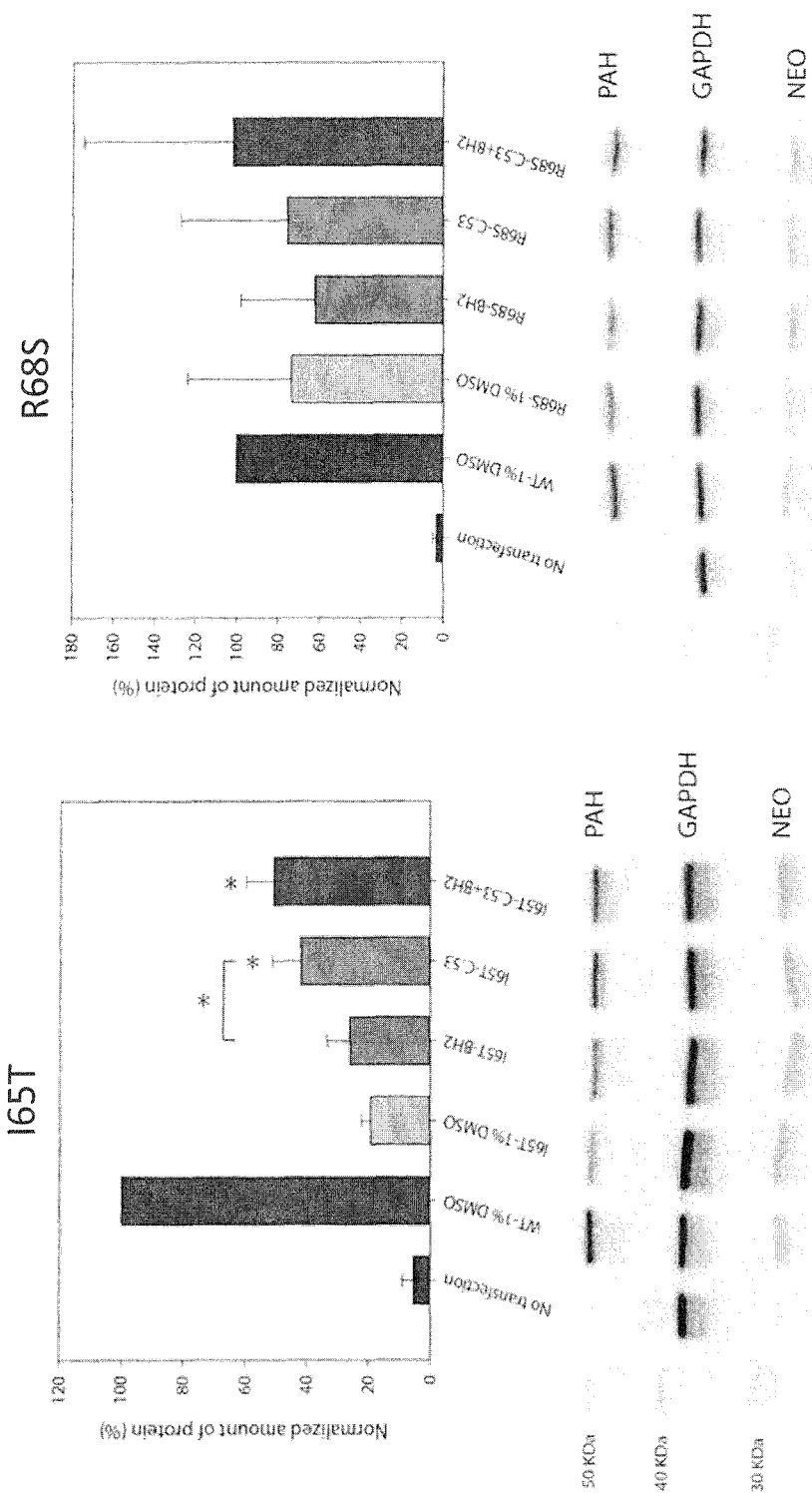
Figures 2C, 2D:
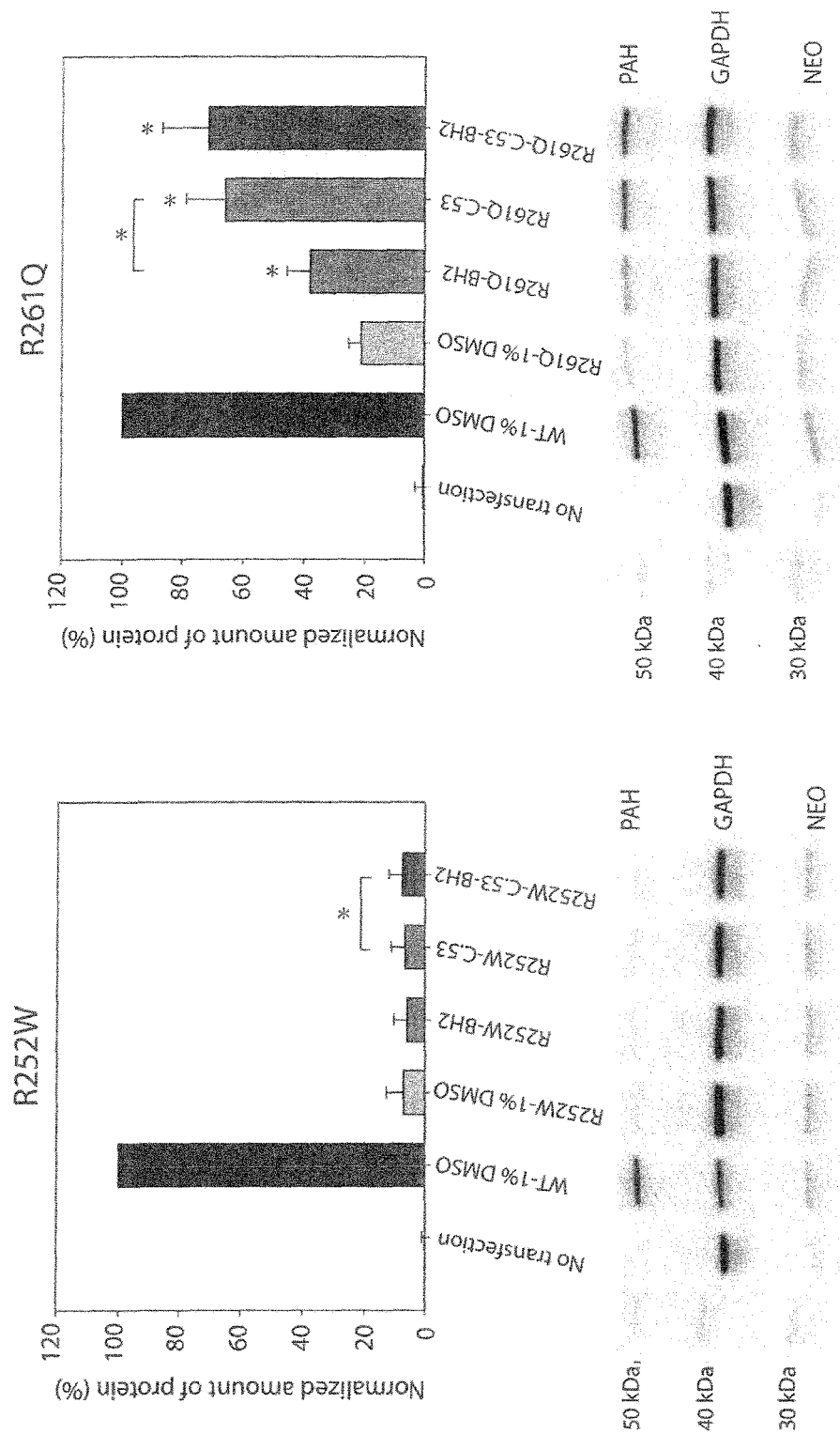
Figure 2F:
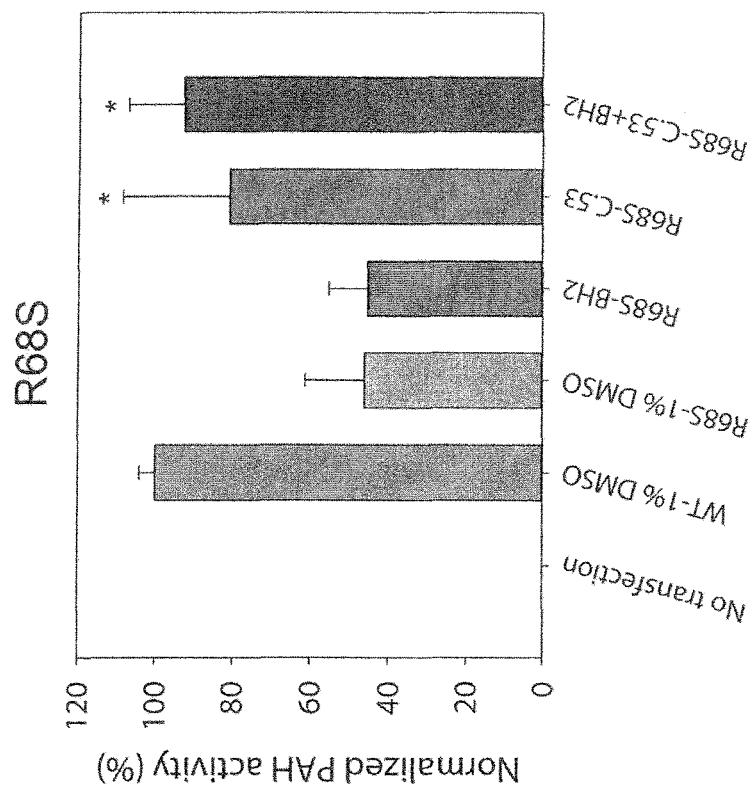
Figure 2E:
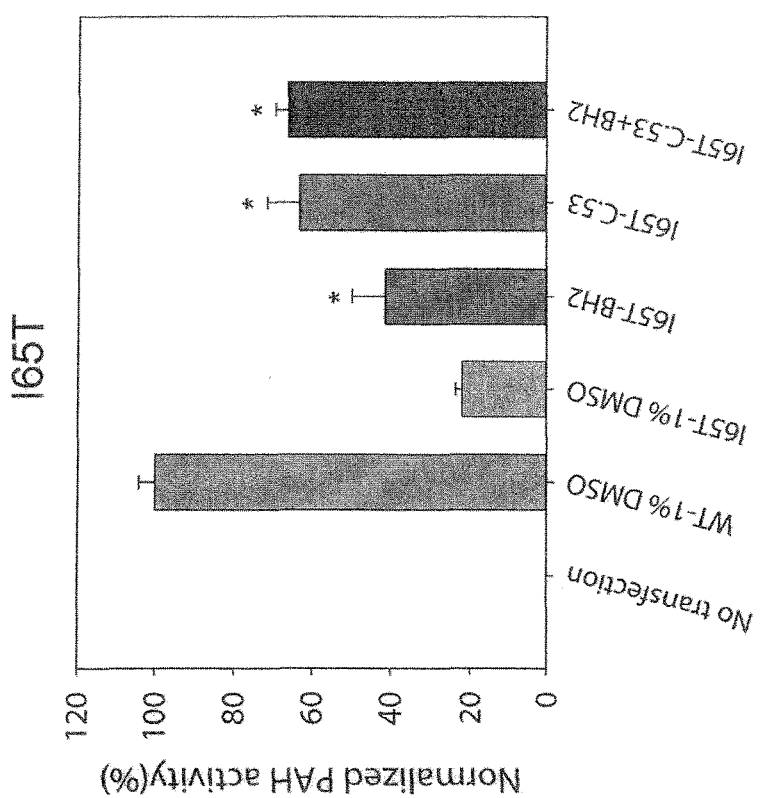
Figure 2H:
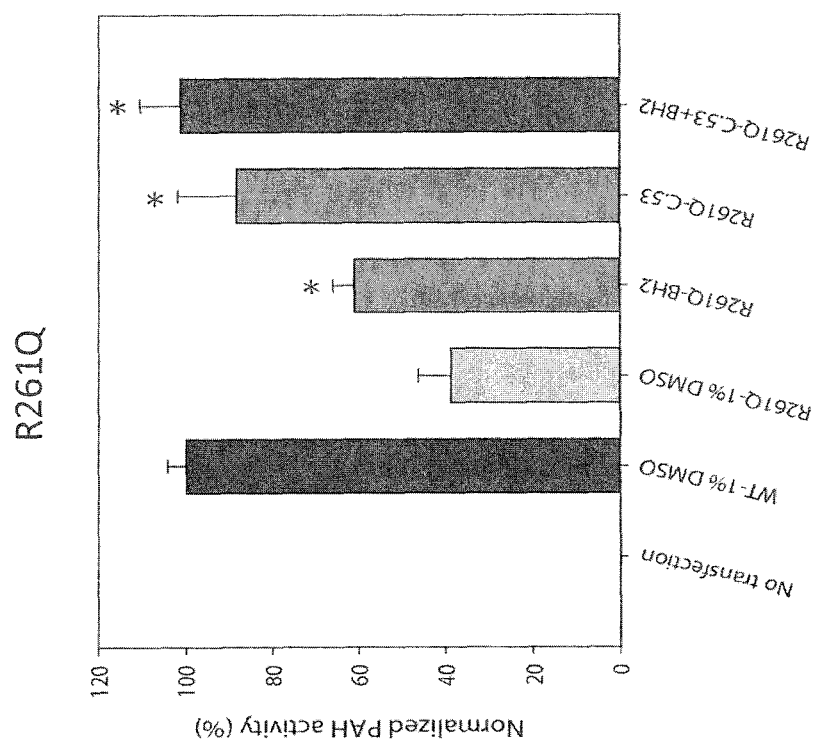
Figure 2G:
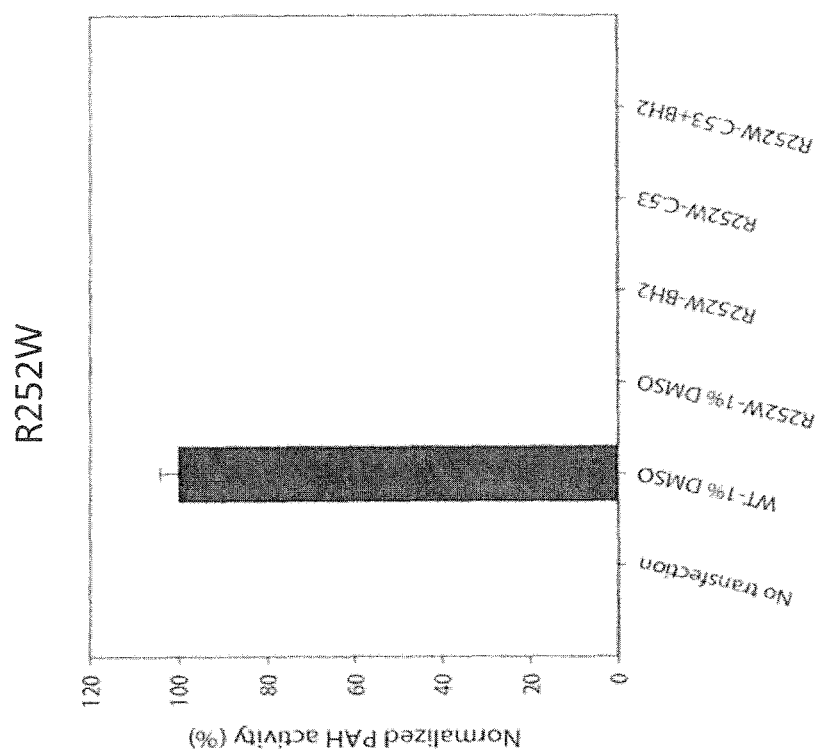

Except for R252W-PAH, which showed an activity below the assay detection limit, the DMSO-controls of the PKU mutants presented measureable immunoreactive levels (25-70% of WT) and activities (25-50% of WT). In the presence of compound 53 both hPAH protein levels and PAH activity of cells expressing mutants I65T and R261Q were greatly increased. $BH_2$ also increased protein and activity of the same cells, and trends for additive effects for Compound 53 and $BH_2$ were also observed. An effect of Compound 53 on the activity of cells expressing R68S was also measured, but neither the compound or $BH_4$ affected the severe mutant R252W, although we observed a little stimulation of the protein content when cells expressing this mutant were grown with both compound and cofactor analogue together (FIG. 2D).

Effect of Compound 53 on the hPAH Activity

Once we demonstrated the good effect of Compound 53 in stimulating PAH protein and activity in cells expressing hPAH (both WT and PKU mutants) we studied in more detail the effect of the compound on the steady state enzyme kinetics (FIG. 3). For the DMSO control enzyme $S_{0.5}$(L-Phe) and $K_m(BH_4)$ values are in accordance with those obtained in previous studies for the full length enzyme, although the activity values and $V_{max}$ are higher. As we can observe in the phenylalanine titration graph (FIG. 3A,D), the compound does not affect the kinetic parameters for the substrate ($V_{max}$ and $S_{0.5}$), or the characteristic positive cooperativity for L-Phe also remains unmodified. On the other hand, we observed a small inhibitory effect of the compound in the $BH_4$-concentracion curve, resulting in decreased $V_{max}$ and $K_m$ for the cofactor (FIG. 3B,D), indicative of an uncompetitive inhibition. The results suggest that the compound does not affect the binding of L-Phe or the activating regulatory conformational change caused by the substrate. The uncompetitive mechanism towards $BH_4$ indicates that compound 53 binds tighter to the transition state than to the free enzyme and the sequestering of the enzyme-$BH_4$ complex results in apparent decrease of $K_m$ by the Chatelier principle.

When the effect of the compound is tested with a truncated form of the enzyme, i.e. the dimeric hPAH $\Delta$N102/$\Delta$C24, lacking both the regulatory domain and the tetramerization motif, compound 53 did not change the $V_{max}$ or $K_m$-values for $BH_4$ (FIG. 3C,D), indicating no effect on the binding of $BH_4$ in this enzyme form.

Derivatization of Compound 53

Compound 53 is a known antibacterial agent, trimethoprim (TMP). It binds to bacterial variants of dihydrofolate reductase (DHFR) with nM affinity and is thus a potent inhibitor for this enzyme. To avoid inhibition of DHFR using Compound 53 for PKU treatment we set out to identify compound analogues with reduced affinity for DHFR while retaining PAH efficacy. As a first step we aimed at characterizing the chemical features of Compound 53 imperative for the stabilization of PAH. An initial search of commercially available compounds was carried out as described above. All compounds showing a Tanimoto coefficient >0.5 towards Compound 53 were selected for manual inspections. A final selection of 11 compounds (with identifiers c53.1-c53.11) was made with the objective of determining the efficacy of individual atoms in the structure as well as determining the efficacy of both ring structures of Compound 53 to stabilize PAH (FIG. 4). Of the 11 selected compounds, 3 compounds carried the same chemical scaffold with only minor changes to the structure (≤3 atom substitutions; group 1); 4 compounds retained the chemical scaffold, but included a larger number of atom substitutions (>3 atom substitutions; group 2); and another 4 compounds obtained a different chemical scaffold but keeping certain chemical features (group 3).

After initial testing of these first 11 analogues we identified additionally 13 compounds of a particularly potent analogue (c53.10). These compounds share the same scaffold as Compound 53, but contain a fused ring system on the pyrimidine ring (see FIGS. 7 and 8).

The ChEMBL database contains bioactivity data for large numbers of small molecules. We utilized this data set to identify the chemical features imperative for DHFR inhibition for compounds with the same scaffold as Compound 53. We found that all compounds similar to Compound 53 with an unmodified pyrimidine ring showed strong inhibition of bacterial DHFR. This is supported by the X-ray structure of DHFR in complex with Compound 53 (PDB ID 1DG5) where Asp27 forms a double H-bond with the pyrimidine ring of Compound 53. Consequently, compounds with substitutions of specific H-bond donor atoms of the pyrimidine ring show weaker affinity towards DHFR (see FIG. 5 for selected compounds). We identified 5 compounds with the same chemical scaffold as Compound 53 with substitutions on the pyrimidine ring affecting the affinity towards DHFR. Notably, Compound 53 with one nitrogen of the pyrimidine substituted to a carbon atom (CHEMBL 128600; FIG. 5) shows an IC50 value of 10 mM (the absent methyl group elsewhere in the compound is not believed to be material to binding affinity).

Example 2

Screening and Affinity Determination by SPR:

For detailed determination of binding affinity of Compound 53 and derivatives (FIG. 4) SPR was performed on a Biacore T200 (GE Healthcare Life Sciences) at a temperature of 25° C. A hPAH solution at 0.08 µg/µl in a final volume of 200 µl in acetate buffer pH 5.0 was immobilized onto series S sensor chip CM5 by the standard amine coupling procedure at a flow rate of 30 µl/min and PBS-P+ buffer as running buffer aiming for RU 20000. After the coupling reaction the surface of the sensor chip was washed to eliminate unbound species with HBS buffer (0.01 M NaHepes pH 7.4, 0.15 M NaCI) at steady flow of 20 µl/min for 1 hour until the baseline drift was around 0.05 RU/s; note that an early injection of 40 µl dithiothreitol (DTT) 10 mM in HBS allowed for this reduced washing time.

For the screening, compounds were assayed at a concentration of 200 µM, with 5% DMSO in duplicates, including negative controls with 5% DMSO, positive controls, with 200 µM $BH_2$ and solvent correction was also performed. For $K_D$ calculations, a compound concentration 0-500 µM (in 5% DMSO) were applied at otherwise analogous experimental design and analyses were performed using Biacore T200 Evaluation Software, version 2.0 (GE Healthcare Life Sciences).

Results:

All the responses from the compounds of the screening were subjected to blank subtraction (negative control 5% DMSO), molecular weight adjustment and solvent correction to account for differences in bulk response. Next a cut-off value for the screening was selected based on the response of the positive control of our experiments: RU $BH_2+3*SD$ (2.88+3*1.79=8.27). In this manner, from the 11 derivatives of Compound 53 tested (see FIG. 4) we weeded out those compounds with a lower response than 8.27, namely #53.2, #53.9 and #53.11.

In addition and for the rest of the compounds which continued our workflow, binding affinities were determined and the results are shown in the following table. The selected conditions to measure affinity are selected for high throughput measurements, but the affinities are overestimated though the relative $K_D$ for the different compounds are reliable.

TABLE 1

| Compound ID. | $K_D$ (µM) ± SER |
|---|---|
| c53-TMP | 58.5 ± 35.8 |
| c53.1 | 104 ± 14 |
| c53.3 | 860 ± 1377 |
| c53.4 | 45.2 ± 9.1 |
| c53.5 | 370 ± 228 |
| c53.6 | 103 ± 48.8 |
| c53.7 | 6.9 ± 4.9 |
| c53.8 | — |
| c53.10 | 22.9 ± 2.7 |

Interestingly, as highlighted in bold in the table, we were able by our similarity search to find three derivatives that presented a lower $K_D$ value than our initial hit Compound 53 (c53). In other words, c53.4, c53.7 and c53.10, according to these results, would bind with higher affinity towards hPAH with possibly enhanced potency as pharmacological chaperones.

Due to the high potency and alternative structure of c53.10, we identified and bought additionally 13 c53.10 analogues. 7 of these (FIG. 7) have been tested using DSF and all show a $\Delta T_m$ value of ~5° C.

Binding affinities were determined for some further compounds of the invention (derivatives of compounds 53 and 53.10; as shown in FIGS. 7, 9 and 10). The results are shown in Table 2. The methodology used was the same as discussed above.

TABLE 2

| Compound ID. | $K_D$ (µM) ± SER |
|---|---|
| c53.14 | 24.7 ± 12.1 |
| c53.16 | 76.3 ± 26.4 |
| c53.17 | 11.0 ± 3.7 |
| c53.19 | 37.2 ± 23.7 |
| c53.20 | 23.2 ± 11.7 |
| c53.22 | 30.1 ± 6.5 |
| c53.26 | 62.1 ± 30.7 |
| c53.29 | 191 ± 20 |
| c53.31 | 55.9 ± 6.7 |
| c53.32 | 102 ± 11 |
| c53.33 | 182 ± 32 |

TABLE 2-continued

| Compound ID. | $K_D$ (μM) ± SER |
|---|---|
| c53.35 | 23.7 ± 5.0 |
| c53.40 | 11.6 ± 1.6 |
| c53.41 | 12.6 ± 6.4 |

Example 3

Expression Studies in HEK293 Cells Permanently Expressing hPAH:

Human embryonic kidney cells (HEK293; Life Technologies™) permanently expressing WT-hPAH, prepared with the Flp-In system (Life Technologies™) were kindly provided by Per Knappskog, Haukeland University Hospital. About 1 million cells were grown in DMEM medium containing 4.5 g/l glucose, 10% (v/v) fetal calf serum, 0.25 mg/ml gentamycine, 2 mM L-glutamine and 50 μg/ml hygromycin B, and after 24 h medium was changed and the compounds were added at a concentration of 0.04 mg/ml (1% DMSO). Eight hours later, the cells were harvested, and the pellets frozen in dry ice and stored at −80° C. Control experiments revealed no significant effects of 1% DMSO either on cell growth and survival or on PAH activity and immunoreactivity (data not shown). To prepare the cell extracts, the frozen cell pellets were thawed in TBS (+protease inhibitor) buffer and cells were homogenized with 0.1% TX-100, incubated 15 minutes at 4° C. and extracts were clarified by centrifugation 20000 g for 15 minutes at 4° C. Protein concentrations were normalized using a Direct Detect Spectrometer (Merck Millipore).

Results

Five Compound 53 derivatives were further analyzed in HEK293 cell cultures to observe how the activity of hPAH was altered by the presence of these compounds (FIG. 6).

Even though all the derivatives studied increased hPAH with respect to the control, it was c53.4 and c53.10 that reached levels comparable to c53 (around 40% increase).

Example 4

Further tests on derivatives of Compounds 53 and 53.10 to assess enzyme activity were carried out in the same way as set out in Example 3, with the results set out below in Table 3. Some natural variance is seen between the results in FIG. 6 and Table 3 for those compounds which were tested in both experiments.

TABLE 3

| Compound ID | PAH activity-cells (%) |
|---|---|
| c53 | 148 ± 16 |
| c53.1 | 130 ± 8 |
| c53.3 | 112 ± 10 |
| c53.4 | 165 ± 28 |
| c53.6 | 120 ± 12 |
| c53.7 | 119 ± 5 |
| c53.10 | 155 ± 13 |
| c53.14 | 175 ± 23 |
| c53.16 | 146 ± 10 |
| c53.17 | 206 ± 10 |
| c53.19 | 170 ± 17 |
| c53.20 | 206 ± 5 |
| c53.22 | 154 ± 16 |
| c53.26 | 109 ± 5 |
| c53.29 | 155 ± 7 |
| c53.31 | 125 ± 8 |

The invention claimed is:

1. A method of treating hyperphenylalaninemia (HPA) in a subject comprising administering thereto an effective amount of a compound of formula (I)

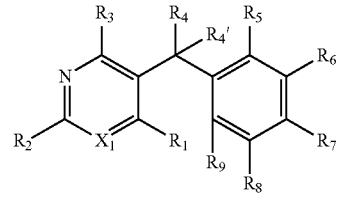

(I)

in which $X_1$ is C or N;

$R_1$, $R_2$, and $R_3$, which may be the same or different, are selected from the group consisting of H, $NH_2$, OH, CN, $NO_2$, SH, halogen, optionally substituted $C_1$-$C_6$ alkyl or $C_2$-$C_6$ alkenyl, optionally substituted $C_1$-$C_6$ heteroalkyl wherein the heteroatoms are one or more N, O or S, optionally substituted $C_1$-$C_6$ thiol, optionally oxidized to —S(O)— or —S(O)$_2$—, optionally substituted $C_1$-$C_6$ aminoalkyl, optionally substituted $C_1$-$C_6$ alkoxy, $(Y)_pCO(Z)_qR_A$ and an aromatic group, optionally containing one or more heteroatoms selected from O, N and S, said aromatic group being optionally substituted, wherein Y and Z are independently selected from O and $N(R_B)$, p and q are independently 0 or 1, $R_A$ is selected from the group consisting of H, optionally substituted $C_1$-$C_6$ alkyl or $C_2$-$C_6$ alkenyl, and optionally substituted $C_1$-$C_6$ heteroalkyl wherein the heteroatoms are one or more N, O or S, and $R_B$ is selected from H and $C_1$-$C_3$ alkyl or cycloalkyl; and $R_4$ and $R_4'$ are independently selected from H, F, optionally substituted $C_1$-$C_6$ alkyl or $C_2$-$C_6$ alkenyl, optionally substituted phenyl or a 5- or 6-membered heteroaryl group or are fused to form a 3-6 membered aliphatic cyclic group which may contain one or more heteroatoms selected from N, O and S or together form =O or =S; or $R_3$ and $R_4$ are fused to form a 5- or 6-membered ring, preferably a 6-membered ring, and thereby a compound of formula IIa

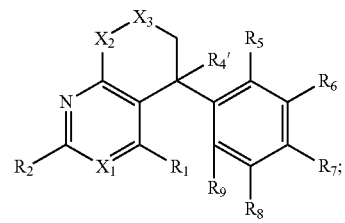

(IIa)

or $R_1$ and $R_4$ are fused to form a 5- or 6-membered ring, preferably a 6-membered ring, and thereby a compound of formula IIb

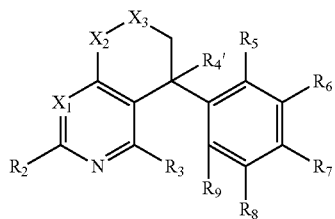

(IIb)

in which
X$_2$ is NR$_{10}$, O or S, wherein R$_{10}$ is H or C$_{1-3}$ alkyl which may be partially or fully fluorinated; and
X$_3$ is a single or double bond, —CO, —SO$_2$ or —CH$_2$—;
R$_5$, R$_6$, R$_7$, R$_8$ and R$_9$, which may be the same or different, are selected from the group consisting of H, OH, SH, halogen, CN, NO$_2$, NH$_2$, optionally substituted C$_1$-C$_6$ alkyl, optionally substituted C$_2$-C$_6$ alkenyl, optionally substituted C$_1$-C$_6$ aminoalkyl, optionally substituted C$_1$-C$_6$ heteroalkyl wherein the hetero atom is N, O or S, optionally substituted C$_1$-C$_6$ alkoxy, optionally substituted benzyloxy, optionally substituted C$_1$-C$_6$ thiol, optionally oxidized to —S(O)— or —S(O)$_2$—, and an aromatic group, optionally containing one or more heteroatoms selected from O, N and S, said aromatic group being optionally substituted,
two of R$_5$, R$_6$, R$_7$, R$_8$ and R$_9$ may together form an optionally substituted carbocyclic or heterocyclic group;
or a pharmaceutically acceptable salt or solvate thereof or a tautomer thereof.

2. The method of claim 1 wherein the substituents of any substituted C$_{2-6}$ alkenyl, C$_1$-C$_6$ alkyl, aminoalkyl, alkoxy, thiol or heteroalkyl group, which may be the same or different, are selected from the following: halogen, CN, OH, NH$_2$, NO$_2$, SH, O, optionally substituted C$_1$-C$_3$ alkyl, optionally substituted C$_2$-C$_3$-alkenyl, optionally substituted C$_1$-C$_3$ alkoxy, optionally substituted C$_1$-C$_3$ thiol, optionally substituted C$_1$-C$_3$ aminoalkyl, optionally substituted C$_1$-C$_3$ heteroalkyl, wherein heteroatoms are selected from N, O or S and a cyclic group which may be aromatic or aliphatic and may be a 4, 5 or 6 membered ring, optionally containing one or more heteroatoms selected from O, N and S, said cyclic group being optionally substituted.

3. The method of claim 2 wherein the substituents of any substituted C$_{2-3}$ alkenyl, C$_{1-3}$ alkyl, aminoalkyl, alkoxy, thiol or heteroalkyl group are selected from: halogen, NH$_2$, OH, SH, O, CN and NO$_2$.

4. The method of claim 1, wherein R$_1$, R$_2$ and R$_3$ are selected from NH$_2$ and OH, preferably wherein one or more of R$_1$, R$_2$ and R$_3$ is NH$_2$.

5. The method of claim 1, wherein R$_2$ is NH$_2$, and either both of R$_1$ and R$_3$ are NH$_2$, or one of R$_1$ or R$_3$ is NH$_2$ and the other is H; or wherein the compound is a compound of formula (IIa) or (IIb), and R$_2$ is NH$_2$ and R$_1$ or R$_3$ is OH.

6. The method of claim 1, wherein R$_5$, R$_6$, R$_7$, R$_8$ and R$_9$ are selected from methoxy, SCH$_3$, OH, Cl, F, or methyl, or two of R$_5$, R$_6$, R$_7$, R$_8$ and R$_9$ together form —O—CH$_2$—O—, —O—CH$_2$—CH$_2$—O— or phenyl.

7. The method of claim 6, wherein R$_5$, R$_6$, R$_7$, R$_8$ and R$_9$ are selected from methoxy and Cl, or two of R$_5$, R$_6$, R$_7$, R$_8$ and R$_9$ together form —O—CH$_2$—O—.

8. The method of claim of 1 wherein R$_4$' is H.

9. The method of claim 1 wherein R$_4$ is H or fused to R$_1$ or R$_3$.

10. The method of claim 1 wherein 1, 2 or 3, preferably 2 or 3 of R$_5$, R$_6$, R$_7$, R$_8$ and R$_9$ are C$_1$-C$_3$ alkoxy, most preferably methoxy.

11. The method of claim 1 wherein two of R$_5$, R$_6$, R$_7$, R$_8$ and R$_9$ together form a 5- or 6-membered ring, preferably with 1 or 2 heteroatoms, most preferably with 2 oxygen atoms.

12. The method of claim 1 wherein X$_3$ is —C(=O).

13. The method of claim 1, wherein X$_1$ is N and X$_2$ is —NH—.

14. The method of claim 1, wherein the compound is selected from

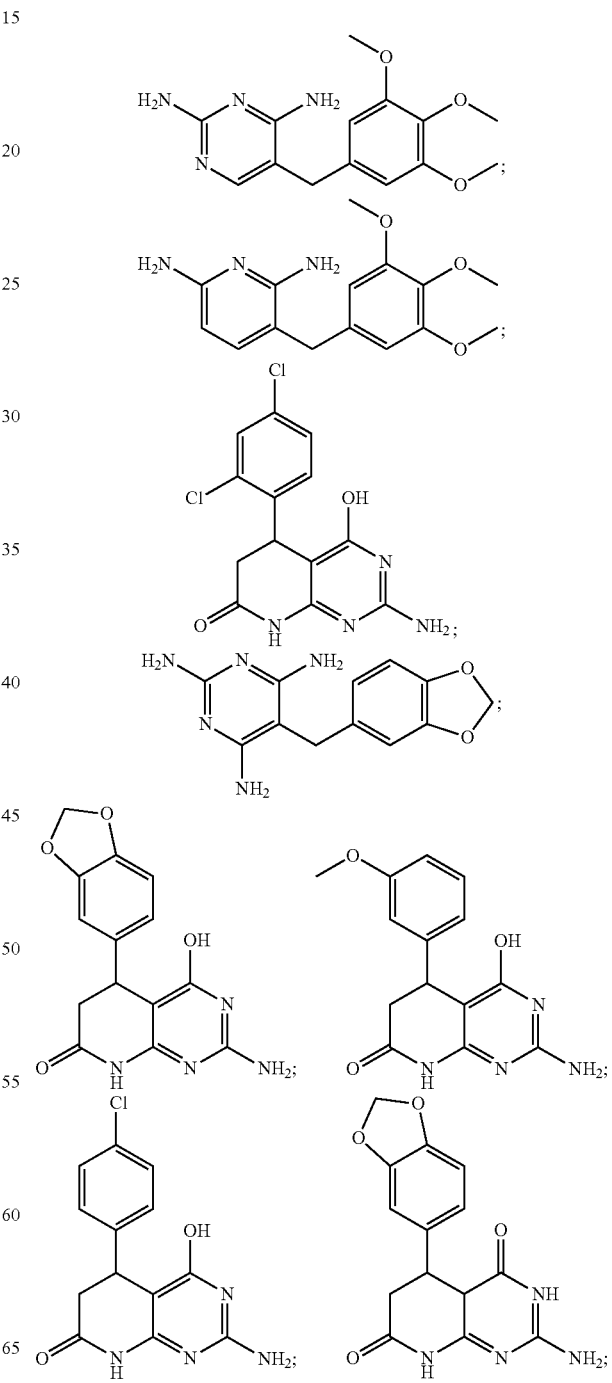

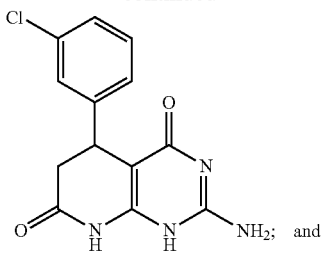

15. The method of claim 1, wherein the hyperphenylalaninemia (HPA) is phenylketonuria (PKU).

16. An in vitro method of stabilising phenylalanine hydroxylase (PAH) which comprises contacting PAH with a compound of formula (I) as defined in claim 1 or a pharmaceutically acceptable salt or solvate thereof.

17. A pharmaceutical pack comprising, not in admixture but for simultaneous or sequential administration, a compound of formula (I) as defined in claim 1, or a pharmaceutically acceptable salt or solvate thereof and a further agent effective in the treatment of HPA.

18. A composition comprising a compound of formula (I) as defined in claim 1, or a pharmaceutically acceptable salt or solvate thereof and a further agent effective in the treatment of HPA.

19. A pack as claimed in claim 17, wherein the further agent is $BH_4$ or an analogue or precursor thereof.

20. The method of claim 1, wherein the compound has essentially no inhibitory effect on dihydrofolate reductase (DHFR).

21. The method of claim 1, wherein the treated condition is mild HPA, mild PKU or classic PKU in a subject exhibiting ≥10% of wild-type PAH activity.

22. A composition as claimed in claim 18, wherein the further agent is $BH_4$ or an analogue or precursor thereof.

* * * * *